(12) United States Patent
Dunki-Jacobs et al.

(10) Patent No.: US 12,064,142 B2
(45) Date of Patent: Aug. 20, 2024

(54) SYSTEMS, DEVICES, AND METHODS FOR PREVENTING OR REDUCING LOSS OF INSUFFLATION DURING A LAPAROSCOPIC SURGICAL PROCEDURE

(71) Applicant: Standard Bariatrics, Inc., Cincinnati, OH (US)

(72) Inventors: Adam R. Dunki-Jacobs, Cincinnati, OH (US); Mark S. Ortiz, Milford, OH (US); Jonathan R. Thompson, Cincinnati, OH (US); Richard P. Nuchols, Williamsburg, OH (US); Caleb J. Hayward, Goshen, OH (US); Robert T. Means, III, Cincinnati, OH (US); Saylan J. Lukas, Cincinnati, OH (US)

(73) Assignee: Standard Bariatrics, Inc., Cincinnati, OH (US)

( * ) Notice: Subject to any disclaimer, the term of this patent is extended or adjusted under 35 U.S.C. 154(b) by 205 days.

(21) Appl. No.: 17/364,146

(22) Filed: Jun. 30, 2021

(65) Prior Publication Data
US 2021/0401462 A1 Dec. 30, 2021

Related U.S. Application Data

(60) Provisional application No. 63/174,065, filed on Apr. 13, 2021, provisional application No. 63/046,153, filed on Jun. 30, 2020.

(51) Int. Cl.
*A61B 17/34* (2006.01)
*A61M 13/00* (2006.01)

(52) U.S. Cl.
CPC ...... *A61B 17/3474* (2013.01); *A61B 17/3421* (2013.01); *A61B 17/3439* (2013.01);
(Continued)

(58) Field of Classification Search
CPC ............ A61B 17/3474; A61B 17/3421; A61B 17/3439; A61B 2017/3443;
(Continued)

(56) References Cited

U.S. PATENT DOCUMENTS

| | | | |
|---|---|---|---|
| 848,126 A | 3/1907 | Roosevelt | |
| 1,413,896 A | 4/1922 | Harold | |

(Continued)

FOREIGN PATENT DOCUMENTS

| | | | |
|---|---|---|---|
| CA | 2663002 A1 | 10/2009 | |
| EP | 140552 A2 | 5/1985 | |

(Continued)

OTHER PUBLICATIONS

De Petz, A; Aseptic Technic of Stomach Resections; 86 Annals of Surgery 388; Sep. 1927; 5 pages.
(Continued)

*Primary Examiner* — Theodore J Stigell

(57) ABSTRACT

Systems and methods for reducing insufflation loss due to gas leakage during a laparoscopic surgical procedure are provided. The surgical procedure includes the use of a surgical instrument having an end effector and a trocar through which the surgical instrument is inserted for access to the abdominal cavity of a patient receiving laparoscopic surgery. The trocar includes a lip, a lip seal disposed within the lip, and a cannula located beneath the lip. The systems and methods reduce or prevent a loss of insufflation when using conventional systems and methods to insert the surgical instrument through a conventional trocar.

16 Claims, 16 Drawing Sheets

(52) U.S. Cl.
CPC .......... *A61B 2017/3443* (2013.01); *A61B 2017/3486* (2013.01); *A61M 13/003* (2013.01)

(58) Field of Classification Search
CPC .......... A61B 2017/3486; A61B 90/40; A61B 2017/3435; A61B 2017/3441; A61B 17/3462; A61M 13/003
See application file for complete search history.

(56) References Cited

U.S. PATENT DOCUMENTS

| | | |
|---|---|---|
| 2,659,371 A | 11/1953 | Schnee |
| 2,686,520 A | 8/1954 | Jarvis et al. |
| 3,017,637 A | 1/1962 | Sampson |
| 3,490,675 A | 1/1970 | Green et al. |
| 3,551,987 A | 1/1971 | Wilkinson |
| 3,877,434 A | 4/1975 | Ferguson |
| 4,216,891 A | 8/1980 | Behlke |
| 4,269,190 A | 5/1981 | Behney |
| 4,319,576 A | 3/1982 | Rothfuss |
| 4,354,628 A | 10/1982 | Green |
| 4,442,964 A | 4/1984 | Becht |
| 4,458,681 A | 7/1984 | Hopkins |
| 4,494,057 A | 1/1985 | Hotta |
| 4,520,817 A | 6/1985 | Green |
| 4,527,724 A | 7/1985 | Chow et al. |
| 4,558,699 A | 12/1985 | Bashour |
| 4,605,001 A | 8/1986 | Rothfuss et al. |
| 4,605,004 A | 8/1986 | Di Giovanni et al. |
| 4,608,981 A | 9/1986 | Rothfuss et al. |
| 4,610,383 A | 9/1986 | Rothfuss et al. |
| 4,617,928 A | 10/1986 | Alfranca |
| 4,632,290 A | 12/1986 | Green et al. |
| 4,633,861 A | 1/1987 | Chow et al. |
| 4,676,774 A | 6/1987 | Semm et al. |
| 4,679,557 A | 7/1987 | Opie et al. |
| 4,705,038 A | 11/1987 | Sjostrom et al. |
| 4,784,137 A | 11/1988 | Kulik et al. |
| 4,803,985 A | 2/1989 | Hill |
| 4,819,853 A | 4/1989 | Green |
| 4,848,637 A | 7/1989 | Pruitt |
| 4,930,503 A | 6/1990 | Pruitt |
| 4,935,006 A | 6/1990 | Hasson |
| 4,941,623 A | 7/1990 | Pruitt |
| 4,951,861 A | 8/1990 | Schulze et al. |
| 4,976,721 A | 12/1990 | Blasnik et al. |
| 4,978,049 A | 12/1990 | Green |
| 5,040,715 A | 8/1991 | Green et al. |
| 5,136,220 A | 8/1992 | Philipp |
| 5,152,744 A | 10/1992 | Krause et al. |
| 5,176,651 A | 1/1993 | Allgood et al. |
| 5,205,459 A | 4/1993 | Brinkerhoff et al. |
| 5,219,111 A | 6/1993 | Bilotti et al. |
| 5,221,036 A | 6/1993 | Takase |
| 5,222,961 A | 6/1993 | Nakao et al. |
| 5,258,009 A | 11/1993 | Conners |
| 5,295,977 A | 3/1994 | Cohen et al. |
| 5,307,976 A | 5/1994 | Olson et al. |
| 5,308,576 A | 5/1994 | Green et al. |
| 5,312,410 A | 5/1994 | Miller et al. |
| 5,327,914 A | 7/1994 | Shlain |
| 5,333,772 A | 8/1994 | Rothfuss et al. |
| 5,345,949 A | 9/1994 | Shlain |
| 5,389,098 A | 2/1995 | Tsuruta et al. |
| 5,395,030 A | 3/1995 | Kuramoto et al. |
| 5,395,034 A | 3/1995 | Allen et al. |
| 5,413,267 A | 5/1995 | Solyntjes et al. |
| 5,415,334 A | 5/1995 | Williamson et al. |
| 5,431,323 A | 7/1995 | Smith et al. |
| 5,443,475 A | 8/1995 | Auerbach et al. |
| 5,452,836 A | 9/1995 | Huitema et al. |
| 5,452,837 A | 9/1995 | Williamson et al. |
| 5,456,401 A | 10/1995 | Green et al. |
| 5,465,895 A | 11/1995 | Knodel et al. |
| 5,465,896 A | 11/1995 | Allen et al. |
| 5,469,840 A | 11/1995 | Tanii et al. |
| 5,470,006 A | 11/1995 | Rodak |
| 5,470,009 A | 11/1995 | Rodak |
| 5,480,089 A | 1/1996 | Blewett |
| 5,485,952 A | 1/1996 | Fontayne |
| 5,487,500 A | 1/1996 | Knodel et al. |
| 5,496,333 A | 3/1996 | Sackier et al. |
| 5,503,638 A | 4/1996 | Cooper et al. |
| 5,507,426 A | 4/1996 | Young et al. |
| 5,507,773 A | 4/1996 | Huitema et al. |
| 5,514,098 A | 5/1996 | Pfoslgraf et al. |
| 5,531,744 A | 7/1996 | Nardella et al. |
| 5,549,621 A | 8/1996 | Bessler et al. |
| 5,551,622 A | 9/1996 | Yoon |
| 5,554,169 A | 9/1996 | Green et al. |
| 5,560,530 A | 10/1996 | Bolanos et al. |
| 5,562,702 A | 10/1996 | Huitema et al. |
| 5,571,116 A | 11/1996 | Bolanos et al. |
| 5,571,131 A | 11/1996 | Ek et al. |
| 5,586,711 A | 12/1996 | Plyley et al. |
| 5,597,107 A | 1/1997 | Knodel et al. |
| 5,630,540 A | 5/1997 | Blewett |
| 5,632,432 A | 5/1997 | Schulze et al. |
| 5,636,780 A | 6/1997 | Green et al. |
| 5,655,698 A | 8/1997 | Yoon |
| 5,662,667 A | 9/1997 | Knodel |
| 5,676,674 A | 10/1997 | Bolanos et al. |
| 5,689,159 A | 11/1997 | Culp et al. |
| 5,697,542 A | 12/1997 | Knodel et al. |
| 5,702,409 A | 12/1997 | Rayburn et al. |
| 5,704,534 A | 1/1998 | Huitema et al. |
| 5,707,369 A | 1/1998 | Vaitekunas et al. |
| 5,732,871 A | 3/1998 | Clark et al. |
| 5,762,256 A | 6/1998 | Mastri et al. |
| 5,779,130 A | 7/1998 | Alesi et al. |
| 5,779,132 A | 7/1998 | Knodel et al. |
| 5,782,396 A | 7/1998 | Mastri et al. |
| 5,797,538 A | 8/1998 | Heaton et al. |
| 5,810,240 A | 9/1998 | Robertson |
| 5,814,055 A | 9/1998 | Knodel et al. |
| 5,819,240 A | 10/1998 | Kara |
| 5,820,009 A | 10/1998 | Melling et al. |
| 5,865,361 A | 2/1999 | Milliman et al. |
| 5,868,760 A | 2/1999 | Mcguckin, Jr. |
| 5,871,135 A | 2/1999 | Williamson IV et al. |
| 5,901,895 A | 5/1999 | Heaton et al. |
| 5,902,312 A | 5/1999 | Frater et al. |
| 5,954,259 A | 9/1999 | Viola et al. |
| 5,964,394 A | 10/1999 | Robertson |
| 5,980,248 A | 11/1999 | Kusakabe et al. |
| 5,988,479 A | 11/1999 | Palmer |
| 6,032,849 A | 3/2000 | Mastri et al. |
| 6,048,330 A | 4/2000 | Atala |
| 6,099,551 A | 8/2000 | Gabbay |
| 6,264,087 B1 | 7/2001 | Whitman |
| 6,270,507 B1 | 8/2001 | Callicrate |
| 6,315,184 B1 | 11/2001 | Whitman |
| 6,325,810 B1 | 12/2001 | Hamilton et al. |
| 6,345,754 B1 | 2/2002 | Jeng |
| 6,439,541 B1 * | 8/2002 | Nosel ............... A61B 17/3498 251/149.1 |
| 6,488,196 B1 | 12/2002 | Fenton |
| 6,505,768 B2 | 1/2003 | Whitman |
| 6,511,490 B2 | 1/2003 | Robert |
| 6,616,446 B1 | 9/2003 | Schmid |
| 6,716,233 B1 | 4/2004 | Whitman |
| 6,769,590 B2 | 8/2004 | Vresh et al. |
| 6,793,652 B1 | 9/2004 | Whitman et al. |
| 6,835,199 B2 | 12/2004 | Mcguckin et al. |
| RE38,708 E | 3/2005 | Bolanos et al. |
| 6,953,138 B1 | 10/2005 | Dworak et al. |
| 6,978,921 B2 | 12/2005 | Shelton, IV et al. |
| 6,986,451 B1 | 1/2006 | Mastri et al. |
| 6,988,649 B2 | 1/2006 | Shelton, IV et al. |
| 7,025,791 B2 | 4/2006 | Levine et al. |
| 7,032,799 B2 | 4/2006 | Viola et al. |
| 7,037,344 B2 | 5/2006 | Kagan et al. |
| 7,044,353 B2 | 5/2006 | Mastri et al. |
| 7,070,083 B2 | 7/2006 | Jankowski |

(56) References Cited

U.S. PATENT DOCUMENTS

| | | |
|---|---|---|
| 7,128,253 B2 | 10/2006 | Mastri et al. |
| 7,134,587 B2 | 11/2006 | Schwemberger et al. |
| 7,175,648 B2 | 2/2007 | Nakao |
| 7,207,472 B2 | 4/2007 | Wukusick et al. |
| 7,225,964 B2 | 6/2007 | Mastri et al. |
| 7,229,428 B2 | 6/2007 | Gannoe et al. |
| 7,235,089 B1 | 6/2007 | Mcguckin, Jr. |
| 7,258,262 B2 | 8/2007 | Mastri et al. |
| 7,278,562 B2 | 10/2007 | Mastri et al. |
| 7,278,563 B1 | 10/2007 | Green |
| 7,288,100 B2 | 10/2007 | Molina Trigueros |
| 7,308,998 B2 | 12/2007 | Mastri et al. |
| RE40,237 E | 4/2008 | Bilotti et al. |
| 7,398,908 B2 | 7/2008 | Holsten et al. |
| 7,401,721 B2 | 7/2008 | Holsten et al. |
| 7,404,508 B2 | 7/2008 | Smith et al. |
| 7,407,075 B2 | 8/2008 | Holsten et al. |
| 7,407,076 B2 | 8/2008 | Racenet et al. |
| 7,422,138 B2 | 9/2008 | Bilotti et al. |
| 7,434,716 B2 | 10/2008 | Viola |
| 7,434,717 B2 | 10/2008 | Shelton, IV et al. |
| 7,438,209 B1 | 10/2008 | Hess et al. |
| 7,455,676 B2 | 11/2008 | Holsten et al. |
| 7,467,740 B2 | 12/2008 | Shelton, IV et al. |
| 7,472,815 B2 | 1/2009 | Shelton, IV et al. |
| 7,481,349 B2 | 1/2009 | Holsten et al. |
| 7,500,979 B2 | 3/2009 | Hueil et al. |
| 7,506,791 B2 | 3/2009 | Omaits et al. |
| 7,510,107 B2 | 3/2009 | Timm et al. |
| 7,549,564 B2 | 6/2009 | Boudreaux |
| 7,549,654 B2 | 6/2009 | Anderson et al. |
| 7,565,993 B2 | 7/2009 | Milliman et al. |
| 7,588,175 B2 | 9/2009 | Timm et al. |
| 7,588,176 B2 | 9/2009 | Timm et al. |
| 7,588,177 B2 | 9/2009 | Racenet |
| 7,604,151 B2 | 10/2009 | Hess et al. |
| 7,617,961 B2 | 11/2009 | Viola |
| 7,635,074 B2 | 12/2009 | Olson et al. |
| 7,641,091 B2 | 1/2010 | Olson et al. |
| 7,645,285 B2 | 1/2010 | Cosgrove et al. |
| 7,658,312 B2 | 2/2010 | Vidal et al. |
| 7,665,647 B2 | 2/2010 | Shelton, IV et al. |
| 7,669,746 B2 | 3/2010 | Shelton, IV |
| 7,669,747 B2 | 3/2010 | Weisenburgh et al. |
| 7,673,781 B2 | 3/2010 | Swayze et al. |
| 7,673,782 B2 | 3/2010 | Hess et al. |
| 7,690,547 B2 | 4/2010 | Racenet et al. |
| 7,694,864 B2 | 4/2010 | Okada et al. |
| 7,704,264 B2 | 4/2010 | Ewers et al. |
| 7,708,684 B2 | 5/2010 | Demarais et al. |
| 7,717,312 B2 | 5/2010 | Beetel |
| 7,726,537 B2 | 6/2010 | Olson et al. |
| 7,726,538 B2 | 6/2010 | Holsten et al. |
| 7,726,539 B2 | 6/2010 | Holsten et al. |
| 7,731,072 B2 | 6/2010 | Timm et al. |
| 7,735,703 B2 | 6/2010 | Morgan et al. |
| 7,744,613 B2 | 6/2010 | Ewers et al. |
| 7,758,493 B2 | 7/2010 | Gingras |
| 7,770,774 B2 | 8/2010 | Mastri et al. |
| 7,775,967 B2 | 8/2010 | Gertner |
| D624,182 S | 9/2010 | Thouement |
| 7,793,812 B2 | 9/2010 | Moore et al. |
| 7,794,475 B2 | 9/2010 | Hess et al. |
| 7,815,092 B2 | 10/2010 | Whitman et al. |
| 7,819,896 B2 | 10/2010 | Racenet |
| 7,828,188 B2 | 11/2010 | Jankowski |
| 7,837,079 B2 | 11/2010 | Holsten et al. |
| 7,846,149 B2 | 12/2010 | Jankowski |
| 7,857,184 B2 | 12/2010 | Viola |
| 7,866,525 B2 | 1/2011 | Scirica |
| 7,866,528 B2 | 1/2011 | Olson et al. |
| 7,871,416 B2 | 1/2011 | Phillips |
| 7,891,531 B1 | 2/2011 | Ward |
| 7,891,533 B2 | 2/2011 | Green et al. |
| 7,913,893 B2 | 3/2011 | Mastri et al. |
| 7,918,869 B2 | 4/2011 | Saadat et al. |
| 7,934,630 B2 | 5/2011 | Shelton, IV et al. |
| 7,955,340 B2 | 6/2011 | Michlitsch et al. |
| 7,959,050 B2 | 6/2011 | Smith et al. |
| 7,963,907 B2 | 6/2011 | Gertner |
| 7,966,799 B2 | 6/2011 | Morgan et al. |
| 7,992,757 B2 | 8/2011 | Wheeler et al. |
| 7,997,469 B2 | 8/2011 | Olson et al. |
| 8,016,176 B2 | 9/2011 | Kasvikis et al. |
| 8,020,741 B2 | 9/2011 | Cole et al. |
| 8,028,884 B2 | 10/2011 | Sniffin et al. |
| 8,033,442 B2 | 10/2011 | Racenet et al. |
| 8,034,077 B2 | 10/2011 | Smith et al. |
| 8,052,697 B2 | 11/2011 | Phillips |
| 8,056,788 B2 | 11/2011 | Mastri et al. |
| 8,061,577 B2 | 11/2011 | Racenet et al. |
| 8,062,236 B2 | 11/2011 | Soltz |
| 8,066,168 B2 | 11/2011 | Vidal et al. |
| 8,070,034 B1 | 12/2011 | Knodel |
| 8,070,036 B1 | 12/2011 | Knodel |
| 8,087,563 B2 | 1/2012 | Milliman et al. |
| 8,091,756 B2 | 1/2012 | Viola |
| 8,096,459 B2 | 1/2012 | Ortiz et al. |
| 8,113,406 B2 | 2/2012 | Holsten et al. |
| 8,132,704 B2 | 3/2012 | Whitman et al. |
| 8,141,762 B2 | 3/2012 | Bedi et al. |
| 8,147,506 B2 | 4/2012 | Ortiz et al. |
| 8,167,186 B2 | 5/2012 | Racenet et al. |
| 8,172,122 B2 | 5/2012 | Kasvikis et al. |
| 8,186,560 B2 | 5/2012 | Hess et al. |
| 8,196,795 B2 | 6/2012 | Moore et al. |
| 8,205,780 B2 | 6/2012 | Sorrentino et al. |
| 8,210,415 B2 | 7/2012 | Ward |
| 8,216,159 B1 | 7/2012 | Leiboff |
| 8,220,690 B2 | 7/2012 | Hess et al. |
| 8,226,602 B2 | 7/2012 | Quijana et al. |
| 8,245,898 B2 | 8/2012 | Smith et al. |
| 8,252,009 B2 | 8/2012 | Weller et al. |
| 8,256,655 B2 | 9/2012 | Sniffin et al. |
| 8,276,801 B2 | 10/2012 | Zemlok et al. |
| 8,292,153 B2 | 10/2012 | Jankowski |
| 8,308,725 B2 | 11/2012 | Bell et al. |
| 8,317,070 B2 | 11/2012 | Hueil et al. |
| 8,322,455 B2 | 12/2012 | Shelton, IV et al. |
| 8,328,061 B2 | 12/2012 | Kasvikis |
| 8,328,064 B2 | 12/2012 | Racenet et al. |
| 8,343,175 B2 | 1/2013 | Ewers et al. |
| 8,348,127 B2 | 1/2013 | Marczyk |
| 8,348,129 B2 | 1/2013 | Bedi et al. |
| 8,348,130 B2 | 1/2013 | Shah et al. |
| 8,348,131 B2 | 1/2013 | Omaits et al. |
| 8,353,436 B2 | 1/2013 | Kasvikis |
| 8,360,297 B2 | 1/2013 | Shelton, IV et al. |
| 8,365,973 B1 | 2/2013 | White et al. |
| 8,365,976 B2 | 2/2013 | Hess et al. |
| 8,382,775 B1 | 2/2013 | Bender et al. |
| 8,393,513 B2 | 3/2013 | Jankowski |
| 8,393,514 B2 | 3/2013 | Shelton, IV et al. |
| 8,403,956 B1 | 3/2013 | Thompson et al. |
| 8,408,442 B2 | 4/2013 | Racenet et al. |
| 8,424,739 B2 | 4/2013 | Racenet et al. |
| 8,439,244 B2 | 5/2013 | Holcomb et al. |
| 8,439,246 B1 | 5/2013 | Knodel |
| 8,449,460 B2 * | 5/2013 | Duke ............... A61B 17/3462 600/208 |
| 8,449,560 B2 | 5/2013 | Roth et al. |
| 8,453,912 B2 | 6/2013 | Mastri et al. |
| 8,453,914 B2 | 6/2013 | Laurent et al. |
| 8,464,923 B2 | 6/2013 | Shelton, IV |
| 8,465,507 B2 | 6/2013 | Cosgrove et al. |
| 8,469,252 B2 | 6/2013 | Holcomb et al. |
| 8,469,977 B2 | 6/2013 | Balbierz et al. |
| 8,479,969 B2 | 7/2013 | Shelton, IV |
| 8,485,412 B2 | 7/2013 | Shelton, IV et al. |
| 8,496,155 B2 | 7/2013 | Knodel |
| 8,496,156 B2 | 7/2013 | Sniffin et al. |
| 8,499,993 B2 | 8/2013 | Shelton, IV et al. |
| 8,523,041 B2 | 9/2013 | Ishitsuki et al. |
| 8,529,585 B2 | 9/2013 | Jacobs et al. |

(56) References Cited

U.S. PATENT DOCUMENTS

| | | |
|---|---|---|
| 8,540,128 B2 | 9/2013 | Shelton, IV et al. |
| 8,540,130 B2 | 9/2013 | Moore et al. |
| 8,544,712 B2 | 10/2013 | Jankowski |
| 8,561,872 B2 | 10/2013 | Wheeler et al. |
| 8,573,465 B2 | 11/2013 | Shelton, IV |
| 8,574,243 B2 | 11/2013 | Saadat et al. |
| 8,579,176 B2 | 11/2013 | Smith et al. |
| 8,579,178 B2 | 11/2013 | Holsten et al. |
| 8,590,762 B2 | 11/2013 | Hess et al. |
| 8,596,513 B2 | 12/2013 | Olson et al. |
| 8,608,043 B2 | 12/2013 | Scirica |
| 8,608,046 B2 | 12/2013 | Laurent et al. |
| 8,613,384 B2 | 12/2013 | Pastorelli et al. |
| 8,616,431 B2 | 12/2013 | Timm et al. |
| 8,617,185 B2 | 12/2013 | Bonutti et al. |
| 8,628,544 B2 | 1/2014 | Farascioni |
| 8,628,547 B2 | 1/2014 | Weller et al. |
| 8,647,350 B2 | 2/2014 | Mohan et al. |
| 8,663,245 B2 | 3/2014 | Francischelli et al. |
| 8,668,130 B2 | 3/2014 | Hess et al. |
| 8,672,208 B2 | 3/2014 | Hess et al. |
| 8,672,830 B2 | 3/2014 | Dlugos, Jr. et al. |
| 8,701,958 B2 | 4/2014 | Shelton, IV et al. |
| 8,714,429 B2 | 5/2014 | Demmy |
| 8,720,766 B2 | 5/2014 | Hess et al. |
| 8,727,197 B2 | 5/2014 | Hess et al. |
| 8,727,199 B2 | 5/2014 | Wenchell |
| 8,733,613 B2 | 5/2014 | Huitema et al. |
| 8,740,035 B2 | 6/2014 | Mastri et al. |
| 8,758,392 B2 | 6/2014 | Crainich |
| 8,763,875 B2 | 7/2014 | Morgan et al. |
| 8,800,838 B2 | 8/2014 | Shelton, IV |
| 8,800,840 B2 | 8/2014 | Jankowski |
| 8,801,732 B2 | 8/2014 | Harris et al. |
| 8,808,161 B2 | 8/2014 | Gregg et al. |
| 8,808,325 B2 | 8/2014 | Hess et al. |
| 8,840,004 B2 | 9/2014 | Holsten et al. |
| 8,852,218 B2 | 10/2014 | Hughett, Sr. et al. |
| 8,864,009 B2 | 10/2014 | Shelton, IV et al. |
| 8,882,766 B2 | 11/2014 | Couture et al. |
| 8,899,465 B2 | 12/2014 | Shelton, IV et al. |
| 8,925,788 B2 | 1/2015 | Hess et al. |
| 8,945,163 B2 | 2/2015 | Voegele et al. |
| 8,956,390 B2 | 2/2015 | Shah et al. |
| 8,973,804 B2 | 3/2015 | Hess et al. |
| 8,978,956 B2 | 3/2015 | Schall et al. |
| 8,991,676 B2 | 3/2015 | Hess et al. |
| 8,991,677 B2 | 3/2015 | Moore et al. |
| 8,998,058 B2 | 4/2015 | Moore et al. |
| 9,011,437 B2 | 4/2015 | Woodruff et al. |
| 9,016,541 B2 | 4/2015 | Viola et al. |
| 9,033,203 B2 | 5/2015 | Woodard, Jr. et al. |
| 9,050,084 B2 | 6/2015 | Schmid et al. |
| 9,066,721 B2 | 6/2015 | Ichihara et al. |
| 9,084,600 B1 | 7/2015 | Knodel et al. |
| 9,084,601 B2 | 7/2015 | Moore et al. |
| 9,095,339 B2 | 8/2015 | Moore et al. |
| 9,113,862 B2 | 8/2015 | Morgan et al. |
| 9,113,868 B2 | 8/2015 | Felder et al. |
| 9,119,627 B2 | 9/2015 | Cosgrove et al. |
| 9,138,226 B2 | 9/2015 | Racenet et al. |
| 9,149,325 B2 | 10/2015 | Worrell et al. |
| 9,155,528 B2 | 10/2015 | Bender et al. |
| 9,168,039 B1 | 10/2015 | Knodel |
| 9,179,911 B2 | 11/2015 | Morgan et al. |
| 9,180,035 B2 | 11/2015 | Stack et al. |
| 9,211,120 B2 | 12/2015 | Scheib et al. |
| 9,216,019 B2 | 12/2015 | Schmid et al. |
| 9,254,131 B2 | 2/2016 | Soltz et al. |
| 9,289,206 B2 | 3/2016 | Hess et al. |
| 9,289,207 B2 | 3/2016 | Shelton, IV |
| 9,307,981 B2 | 4/2016 | Mikkaichi et al. |
| 9,314,362 B2 | 4/2016 | Bender et al. |
| 9,326,768 B2 | 5/2016 | Shelton, IV |
| 9,339,442 B2 | 5/2016 | Tai et al. |
| 9,345,478 B2 | 5/2016 | Knodel |
| 9,364,225 B2 | 6/2016 | Sniffin et al. |
| 9,370,362 B2 | 6/2016 | Petty et al. |
| 9,398,917 B2 | 7/2016 | Whitfield et al. |
| 9,408,604 B2 | 8/2016 | Shelton, IV et al. |
| 9,433,411 B2 | 9/2016 | Racenet et al. |
| 9,439,541 B2 | 9/2016 | Ito et al. |
| 9,439,633 B2 | 9/2016 | O'Dea |
| 9,498,219 B2 | 11/2016 | Moore et al. |
| 9,549,733 B2 | 1/2017 | Knodel |
| 9,561,032 B2 | 2/2017 | Shelton, IV et al. |
| 9,603,595 B2 | 3/2017 | Shelton, IV et al. |
| 9,603,598 B2 | 3/2017 | Shelton, IV et al. |
| 9,615,952 B2 | 4/2017 | Scott et al. |
| 9,636,114 B2 | 5/2017 | Cole et al. |
| 9,675,355 B2 | 6/2017 | Shelton, IV et al. |
| 9,687,233 B2 | 6/2017 | Fernandez et al. |
| 9,687,237 B2 | 6/2017 | Schmid et al. |
| 9,693,816 B2 | 7/2017 | Orszulak |
| 9,700,321 B2 | 7/2017 | Shelton, IV et al. |
| 9,706,991 B2 | 7/2017 | Hess et al. |
| 9,724,091 B2 | 8/2017 | Shelton, IV et al. |
| 9,724,093 B2 | 8/2017 | Farascioni et al. |
| 9,724,096 B2 | 8/2017 | Thompson et al. |
| 9,730,692 B2 | 8/2017 | Shelton, IV et al. |
| 9,775,613 B2 | 10/2017 | Shelton, IV et al. |
| 9,795,380 B2 | 10/2017 | Shelton, IV et al. |
| 9,801,627 B2 | 10/2017 | Harris et al. |
| 9,801,628 B2 | 10/2017 | Harris et al. |
| 9,801,630 B2 | 10/2017 | Harris et al. |
| 9,808,246 B2 | 11/2017 | Shelton, IV et al. |
| 9,808,257 B2 | 11/2017 | Armenteros et al. |
| 9,820,742 B2 | 11/2017 | Covach et al. |
| 9,827,002 B2 | 11/2017 | Hausen et al. |
| 9,844,370 B2 | 12/2017 | Viola et al. |
| 9,848,873 B2 | 12/2017 | Shelton, IV |
| 9,848,875 B2 | 12/2017 | Aronhalt et al. |
| 9,848,878 B2 | 12/2017 | Racenet et al. |
| 9,855,040 B2 | 1/2018 | Kostrzewski |
| 9,861,366 B2 | 1/2018 | Aranyi |
| 9,872,682 B2 | 1/2018 | Hess et al. |
| 9,901,344 B2 | 2/2018 | Moore et al. |
| 9,901,346 B2 | 2/2018 | Moore et al. |
| 9,913,646 B2 | 3/2018 | Shelton, IV |
| 9,924,947 B2 | 3/2018 | Shelton, IV et al. |
| 9,936,953 B2 | 4/2018 | Thompson et al. |
| 9,937,001 B2 | 4/2018 | Nakamura |
| 9,980,729 B2 | 5/2018 | Moore et al. |
| 9,999,426 B2 | 6/2018 | Moore et al. |
| 9,999,431 B2 | 6/2018 | Shelton, IV et al. |
| 10,004,505 B2 | 6/2018 | Moore et al. |
| 10,045,780 B2 | 8/2018 | Adams et al. |
| 10,085,751 B2 | 10/2018 | Overmyer et al. |
| 10,085,754 B2 | 10/2018 | Sniffin et al. |
| 10,130,360 B2 | 11/2018 | Olson et al. |
| 10,130,363 B2 | 11/2018 | Huitema et al. |
| 10,172,616 B2 | 1/2019 | Murray et al. |
| 10,194,912 B2 | 2/2019 | Scheib et al. |
| 10,226,250 B2 | 3/2019 | Beckman et al. |
| 10,231,734 B2 | 3/2019 | Thompson et al. |
| 10,238,517 B2 | 3/2019 | Gingras |
| 10,245,032 B2 | 4/2019 | Shelton, IV |
| 10,258,334 B2 | 4/2019 | Adams et al. |
| 10,265,073 B2 | 4/2019 | Scheib et al. |
| 10,278,695 B2 | 5/2019 | Milo |
| 10,278,699 B2 | 5/2019 | Thompson et al. |
| 10,278,707 B2 | 5/2019 | Thompson et al. |
| 10,285,712 B2 | 5/2019 | Cosgrove, III et al. |
| 10,285,837 B1 | 5/2019 | Thompson et al. |
| 10,292,706 B2 | 5/2019 | Jankowski |
| 10,307,161 B2 | 6/2019 | Jankowski |
| 10,307,163 B2 | 6/2019 | Moore et al. |
| 10,314,580 B2 | 6/2019 | Scheib et al. |
| 10,314,589 B2 | 6/2019 | Shelton, IV et al. |
| 10,342,538 B2 | 7/2019 | Racenet et al. |
| 10,383,628 B2 | 8/2019 | Kang et al. |
| 10,390,826 B2 | 8/2019 | Badawi |
| 10,405,856 B2 | 9/2019 | Knodel |
| 10,405,860 B2 | 9/2019 | Thompson et al. |

(56) References Cited

U.S. PATENT DOCUMENTS

| | | |
|---|---|---|
| 10,420,559 B2 | 9/2019 | Marczyk et al. |
| 10,420,560 B2 | 9/2019 | Shelton, IV et al. |
| 10,441,283 B1 | 10/2019 | Thompson et al. |
| 10,456,571 B2 | 10/2019 | Cairns |
| 10,470,911 B2 | 11/2019 | Thompson et al. |
| 10,485,540 B2 | 11/2019 | Hodgkinson et al. |
| 10,499,912 B2 | 12/2019 | Scheib et al. |
| 10,537,325 B2 | 1/2020 | Bakos et al. |
| 10,542,986 B2 | 1/2020 | Thompson et al. |
| 10,548,597 B2 | 2/2020 | Dunki-Jacobs et al. |
| 10,610,226 B2 | 4/2020 | Shelton et al. |
| 10,624,638 B2 | 4/2020 | Thompson et al. |
| 10,687,807 B2 | 6/2020 | Simms et al. |
| 10,687,810 B2 | 6/2020 | Shelton, IV et al. |
| 10,687,814 B2 | 6/2020 | Dunki-Jacobs et al. |
| 10,716,564 B2 | 7/2020 | Shelton, IV et al. |
| 10,758,231 B2 | 9/2020 | Harris et al. |
| 10,849,623 B2 | 12/2020 | Dunki-Jacobs et al. |
| 10,912,562 B2 | 2/2021 | Dunki-Jacobs et al. |
| 10,966,721 B2 | 4/2021 | Dunki-Jacobs et al. |
| 10,987,108 B2 | 4/2021 | Thompson et al. |
| 11,173,060 B2 | 11/2021 | Thompson et al. |
| 11,197,672 B2 | 12/2021 | Dunki-Jacobs et al. |
| 2001/0044656 A1 | 11/2001 | Williamson, IV et al. |
| 2002/0143346 A1 | 10/2002 | Mcguckin, Jr. et al. |
| 2003/0125734 A1 | 7/2003 | Mollenauer |
| 2003/0135091 A1 | 7/2003 | Nakazawa et al. |
| 2003/0208209 A1 | 11/2003 | Gambale et al. |
| 2003/0220660 A1 | 11/2003 | Kortenbach et al. |
| 2004/0006351 A1 | 1/2004 | Gannoe et al. |
| 2004/0006372 A1 | 1/2004 | Racenet et al. |
| 2004/0068267 A1 | 4/2004 | Harvie et al. |
| 2004/0181239 A1 | 9/2004 | Dorn et al. |
| 2004/0215216 A1 | 10/2004 | Gannoe et al. |
| 2005/0006432 A1 | 1/2005 | Racenet et al. |
| 2005/0080444 A1 | 4/2005 | Kraemer et al. |
| 2005/0139633 A1 | 6/2005 | Wukusick et al. |
| 2005/0203547 A1 | 9/2005 | Weller et al. |
| 2005/0203548 A1 | 9/2005 | Weller et al. |
| 2005/0256533 A1 | 11/2005 | Roth et al. |
| 2006/0011698 A1 | 1/2006 | Okada et al. |
| 2006/0016853 A1 | 1/2006 | Racenet |
| 2006/0020277 A1 | 1/2006 | Gostout et al. |
| 2006/0036267 A1 | 2/2006 | Saadat et al. |
| 2006/0041270 A1* | 2/2006 | Lenker ............ A61B 17/3439 606/198 |
| 2006/0085030 A1 | 4/2006 | Bettuchi et al. |
| 2006/0151568 A1 | 7/2006 | Weller et al. |
| 2006/0229665 A1 | 10/2006 | Wales et al. |
| 2006/0241692 A1 | 10/2006 | Mcguckin et al. |
| 2007/0004968 A1* | 1/2007 | Bonadio ............ A61B 17/3462 600/208 |
| 2007/0023477 A1 | 2/2007 | Whitman et al. |
| 2007/0027469 A1 | 2/2007 | Smith et al. |
| 2007/0029364 A1 | 2/2007 | Kruszynski et al. |
| 2007/0034666 A1 | 2/2007 | Holsten et al. |
| 2007/0034667 A1 | 2/2007 | Holsten et al. |
| 2007/0039997 A1 | 2/2007 | Mather et al. |
| 2007/0056932 A1 | 3/2007 | Whitman et al. |
| 2007/0075114 A1 | 4/2007 | Shelton et al. |
| 2007/0083233 A1 | 4/2007 | Ortiz et al. |
| 2007/0131732 A1 | 6/2007 | Holsten et al. |
| 2007/0179528 A1 | 8/2007 | Soltz et al. |
| 2007/0194079 A1 | 8/2007 | Hueil et al. |
| 2007/0194080 A1 | 8/2007 | Swayze et al. |
| 2007/0194081 A1 | 8/2007 | Hueil et al. |
| 2007/0213743 A1 | 9/2007 | Mcguckin, Jr. |
| 2007/0246505 A1 | 10/2007 | Pace-Floridia et al. |
| 2007/0262116 A1 | 11/2007 | Hueil et al. |
| 2008/0015631 A1 | 1/2008 | Lee et al. |
| 2008/0023522 A1 | 1/2008 | Olson et al. |
| 2008/0033457 A1 | 2/2008 | Francischelli et al. |
| 2008/0035702 A1 | 2/2008 | Holsten et al. |
| 2008/0041918 A1 | 2/2008 | Holsten et al. |
| 2008/0058716 A1 | 3/2008 | Dubrul et al. |
| 2008/0078800 A1 | 4/2008 | Hess et al. |
| 2008/0082124 A1 | 4/2008 | Hess et al. |
| 2008/0087707 A1 | 4/2008 | Jankowski |
| 2008/0097332 A1 | 4/2008 | Greenhalgh et al. |
| 2008/0149684 A1 | 6/2008 | Viola |
| 2008/0164297 A1 | 7/2008 | Holsten et al. |
| 2008/0169329 A1 | 7/2008 | Shelton et al. |
| 2008/0169332 A1 | 7/2008 | Shelton et al. |
| 2008/0190990 A1 | 8/2008 | Holsten et al. |
| 2008/0203134 A1 | 8/2008 | Shah et al. |
| 2008/0249404 A1 | 10/2008 | Mikkaichi et al. |
| 2008/0275480 A1 | 11/2008 | Jacobs et al. |
| 2008/0294179 A1 | 11/2008 | Balbierz et al. |
| 2008/0308602 A1 | 12/2008 | Timm et al. |
| 2009/0001122 A1 | 1/2009 | Prommersberger et al. |
| 2009/0001130 A1 | 1/2009 | Hess et al. |
| 2009/0012556 A1 | 1/2009 | Boudreaux et al. |
| 2009/0020584 A1 | 1/2009 | Soltz et al. |
| 2009/0078739 A1 | 3/2009 | Viola |
| 2009/0095791 A1 | 4/2009 | Eskaros et al. |
| 2009/0101692 A1 | 4/2009 | Whitman et al. |
| 2009/0134200 A1 | 5/2009 | Tarinelli et al. |
| 2009/0173766 A1 | 7/2009 | Wenchell |
| 2009/0209946 A1 | 8/2009 | Swayze et al. |
| 2009/0209986 A1 | 8/2009 | Stewart et al. |
| 2009/0212088 A1 | 8/2009 | Okada et al. |
| 2009/0255974 A1 | 10/2009 | Viola |
| 2009/0261144 A1 | 10/2009 | Sniffin et al. |
| 2009/0308907 A1 | 12/2009 | Nalagatla et al. |
| 2010/0010512 A1 | 1/2010 | Taylor et al. |
| 2010/0072255 A1 | 3/2010 | Olson et al. |
| 2010/0072258 A1 | 3/2010 | Farascioni et al. |
| 2010/0108739 A1 | 5/2010 | Holsten et al. |
| 2010/0114124 A1 | 5/2010 | Kelleher et al. |
| 2010/0121356 A1 | 5/2010 | Hartmann et al. |
| 2010/0137904 A1 | 6/2010 | Wenchell |
| 2010/0145324 A1 | 6/2010 | Nihalani |
| 2010/0213240 A1 | 8/2010 | Kostrzewski |
| 2010/0256634 A1 | 10/2010 | Voegele et al. |
| 2010/0282820 A1 | 11/2010 | Kasvikis |
| 2010/0331866 A1 | 12/2010 | Surti et al. |
| 2011/0004062 A1 | 1/2011 | Asai et al. |
| 2011/0017800 A1 | 1/2011 | Viola |
| 2011/0036888 A1 | 2/2011 | Pribanic et al. |
| 2011/0046653 A1 | 2/2011 | Addington et al. |
| 2011/0071555 A1 | 3/2011 | Mcbrayer et al. |
| 2011/0084113 A1 | 4/2011 | Bedi et al. |
| 2011/0087169 A1* | 4/2011 | Parihar ............ A61B 17/3474 604/167.03 |
| 2011/0087279 A1 | 4/2011 | Shah et al. |
| 2011/0152895 A1 | 6/2011 | Nyuli et al. |
| 2011/0160752 A1 | 6/2011 | Aguirre |
| 2011/0178454 A1 | 7/2011 | Gagner et al. |
| 2011/0186614 A1 | 8/2011 | Kasvikis |
| 2011/0190791 A1 | 8/2011 | Jacobs et al. |
| 2011/0208211 A1 | 8/2011 | Whitfield et al. |
| 2011/0226837 A1 | 9/2011 | Baxter, III et al. |
| 2011/0278343 A1 | 11/2011 | Knodel et al. |
| 2011/0290851 A1 | 12/2011 | Shelton, IV |
| 2011/0315739 A1 | 12/2011 | Sniffin et al. |
| 2012/0035631 A1 | 2/2012 | Hughett, Sr. et al. |
| 2012/0059400 A1 | 3/2012 | Williamson, IV et al. |
| 2012/0080494 A1 | 4/2012 | Thompson et al. |
| 2012/0116379 A1 | 5/2012 | Yates et al. |
| 2012/0123463 A1 | 5/2012 | Jacobs |
| 2012/0175398 A1 | 7/2012 | Sandborn et al. |
| 2012/0203247 A1 | 8/2012 | Shelton, IV et al. |
| 2012/0234899 A1 | 9/2012 | Scheib et al. |
| 2012/0234900 A1 | 9/2012 | Swayze |
| 2012/0248169 A1 | 10/2012 | Widenhouse et al. |
| 2012/0277525 A1 | 11/2012 | O'Dea |
| 2012/0286022 A1 | 11/2012 | Olson et al. |
| 2012/0289979 A1 | 11/2012 | Eskaros et al. |
| 2013/0062394 A1 | 3/2013 | Smith et al. |
| 2013/0075447 A1 | 3/2013 | Weisenburgh, II et al. |
| 2013/0075450 A1 | 3/2013 | Schmid et al. |
| 2013/0092718 A1 | 4/2013 | Soltz et al. |
| 2013/0105549 A1 | 5/2013 | Holsten et al. |
| 2013/0131440 A1 | 5/2013 | Gabriel |

(56) References Cited

U.S. PATENT DOCUMENTS

| | | |
|---|---|---|
| 2013/0146638 A1 | 6/2013 | Mandakolathur Vasudevan et al. |
| 2013/0146641 A1 | 6/2013 | Shelton, IV et al. |
| 2013/0146642 A1 | 6/2013 | Shelton, IV et al. |
| 2013/0153625 A1 | 6/2013 | Felder et al. |
| 2013/0153634 A1 | 6/2013 | Carter et al. |
| 2013/0153642 A1 | 6/2013 | Felder et al. |
| 2013/0161374 A1 | 6/2013 | Swayze et al. |
| 2013/0165774 A1 | 6/2013 | Nocca |
| 2013/0172929 A1 | 7/2013 | Hess et al. |
| 2013/0193190 A1 | 8/2013 | Carter et al. |
| 2013/0214025 A1 | 8/2013 | Zemlok et al. |
| 2013/0245652 A1 | 9/2013 | Cosgrove et al. |
| 2013/0256372 A1 | 10/2013 | Baxter, III et al. |
| 2013/0256375 A1 | 10/2013 | Shelton, IV et al. |
| 2013/0256377 A1 | 10/2013 | Schmid et al. |
| 2013/0284791 A1 | 10/2013 | Olson et al. |
| 2013/0306704 A1 | 11/2013 | Balbierz et al. |
| 2013/0327809 A1 | 12/2013 | Shelton, IV et al. |
| 2013/0334288 A1 | 12/2013 | Shelton, IV |
| 2013/0341374 A1 | 12/2013 | Shelton, IV et al. |
| 2014/0005678 A1 | 1/2014 | Shelton, IV et al. |
| 2014/0008412 A1 | 1/2014 | Zemlok et al. |
| 2014/0018722 A1 | 1/2014 | Scott et al. |
| 2014/0027493 A1 | 1/2014 | Jankowski |
| 2014/0046345 A1 | 2/2014 | Armenteros et al. |
| 2014/0074131 A1 | 3/2014 | Armenteros et al. |
| 2014/0081176 A1 | 3/2014 | Hassan |
| 2014/0082497 A1 | 3/2014 | Chalouhi et al. |
| 2014/0107698 A1 | 4/2014 | Inge |
| 2014/0110457 A1 | 4/2014 | Zhang et al. |
| 2014/0114121 A1 | 4/2014 | Trivedi |
| 2014/0131418 A1 | 5/2014 | Kostrzewski |
| 2014/0131419 A1 | 5/2014 | Bettuchi |
| 2014/0144968 A1 | 5/2014 | Shelton, IV |
| 2014/0148731 A1 | 5/2014 | Radl et al. |
| 2014/0171744 A1 | 6/2014 | Racenet et al. |
| 2014/0183242 A1 | 7/2014 | Farascioni et al. |
| 2014/0184519 A1 | 7/2014 | Benchenaa et al. |
| 2014/0191015 A1 | 7/2014 | Shelton, IV |
| 2014/0214025 A1 | 7/2014 | Worrell et al. |
| 2014/0231489 A1 | 8/2014 | Balbierz et al. |
| 2014/0239037 A1 | 8/2014 | Boudreaux et al. |
| 2014/0257353 A1 | 9/2014 | Whitman et al. |
| 2014/0263570 A1 | 9/2014 | Hopkins et al. |
| 2014/0276932 A1 | 9/2014 | Williams et al. |
| 2014/0291379 A1 | 10/2014 | Schellin et al. |
| 2015/0048141 A1 | 2/2015 | Felder et al. |
| 2015/0083780 A1 | 3/2015 | Shelton, IV et al. |
| 2015/0133740 A1 | 5/2015 | Dierking et al. |
| 2015/0157318 A1 | 6/2015 | Beardsley et al. |
| 2015/0173746 A1 | 6/2015 | Baxter, III et al. |
| 2015/0173755 A1 | 6/2015 | Baxter, III et al. |
| 2015/0173762 A1 | 6/2015 | Shelton, IV et al. |
| 2015/0209034 A1 | 7/2015 | Viola et al. |
| 2015/0265276 A1 | 9/2015 | Huitema et al. |
| 2015/0297224 A1 | 10/2015 | Hall et al. |
| 2015/0297227 A1 | 10/2015 | Huitema et al. |
| 2015/0320423 A1 | 11/2015 | Aranyi |
| 2015/0351764 A1 | 12/2015 | Shelton, IV |
| 2016/0058447 A1 | 3/2016 | Posada et al. |
| 2016/0058594 A1 | 3/2016 | Armenteros et al. |
| 2016/0066916 A1 | 3/2016 | Overmyer et al. |
| 2016/0067074 A1 | 3/2016 | Thompson et al. |
| 2016/0089148 A1 | 3/2016 | Harris et al. |
| 2016/0166256 A1 | 6/2016 | Baxter, III et al. |
| 2016/0183945 A1 | 6/2016 | Shelton, IV et al. |
| 2016/0199061 A1 | 7/2016 | Shelton, IV et al. |
| 2016/0199088 A1 | 7/2016 | Shelton, IV et al. |
| 2016/0213302 A1 | 7/2016 | Frushour |
| 2016/0235409 A1 | 8/2016 | Shelton, IV et al. |
| 2016/0242768 A1 | 8/2016 | Moore et al. |
| 2016/0242769 A1 | 8/2016 | Moore et al. |
| 2016/0242770 A1 | 8/2016 | Moore et al. |
| 2016/0242783 A1 | 8/2016 | Shelton, IV et al. |
| 2016/0256152 A1 | 9/2016 | Kostrzewski |
| 2016/0262744 A1 | 9/2016 | Milo et al. |
| 2016/0262750 A1 | 9/2016 | Hausen et al. |
| 2016/0262921 A1 | 9/2016 | Balbierz et al. |
| 2016/0270792 A1 | 9/2016 | Sniffin et al. |
| 2016/0287251 A1 | 10/2016 | Shelton, IV |
| 2016/0296272 A1 | 10/2016 | Heard |
| 2016/0324527 A1 | 11/2016 | Thompson et al. |
| 2016/0354085 A1 | 12/2016 | Shelton, IV et al. |
| 2016/0367250 A1 | 12/2016 | Racenet et al. |
| 2017/0007248 A1 | 1/2017 | Shelton, IV et al. |
| 2017/0014125 A1 | 1/2017 | Shelton, IV et al. |
| 2017/0027633 A1 | 2/2017 | Wham et al. |
| 2017/0055981 A1 | 3/2017 | Vendely et al. |
| 2017/0055991 A1 | 3/2017 | Kang |
| 2017/0056016 A1 | 3/2017 | Barton et al. |
| 2017/0086847 A1 | 3/2017 | Dinardo et al. |
| 2017/0095251 A1 | 4/2017 | Thompson et al. |
| 2017/0105728 A1 | 4/2017 | Scheib et al. |
| 2017/0172571 A1 | 6/2017 | Thompson et al. |
| 2017/0231633 A1 | 8/2017 | Marczyk et al. |
| 2017/0290588 A1 | 10/2017 | Thompson et al. |
| 2017/0303952 A1 | 10/2017 | Nativ et al. |
| 2017/0319210 A1 | 11/2017 | Moore et al. |
| 2017/0333041 A1 | 11/2017 | Moore et al. |
| 2017/0360447 A1 | 12/2017 | Armenteros et al. |
| 2017/0367697 A1 | 12/2017 | Shelton, IV et al. |
| 2018/0014826 A1 | 1/2018 | Scheib et al. |
| 2018/0036000 A1 | 2/2018 | Terada et al. |
| 2018/0036005 A1 | 2/2018 | Covach et al. |
| 2018/0092641 A1 | 4/2018 | Aranyi |
| 2018/0168594 A1 | 6/2018 | Shelton, IV et al. |
| 2018/0168620 A1 | 6/2018 | Huang et al. |
| 2018/0168633 A1 | 6/2018 | Shelton, IV et al. |
| 2018/0199939 A1 | 7/2018 | Thompson et al. |
| 2018/0199941 A1 | 7/2018 | Thompson et al. |
| 2018/0235625 A1 | 8/2018 | Shelton, IV et al. |
| 2018/0235626 A1 | 8/2018 | Shelton, IV et al. |
| 2018/0280020 A1 | 10/2018 | Hess et al. |
| 2018/0317905 A1 | 11/2018 | Olson et al. |
| 2019/0000455 A1 | 1/2019 | Adams et al. |
| 2019/0046186 A1 | 2/2019 | Dunki-Jacobs et al. |
| 2019/0046189 A1 | 2/2019 | Dunki-Jacobs et al. |
| 2019/0046190 A1 | 2/2019 | Dunki-Jacobs et al. |
| 2019/0046191 A1 | 2/2019 | Dunki-Jacobs et al. |
| 2019/0046192 A1 | 2/2019 | Dunki-Jacobs et al. |
| 2019/0046193 A1 | 2/2019 | Dunki-Jacobs et al. |
| 2019/0105042 A1 | 4/2019 | Huitema et al. |
| 2019/0133577 A1 | 5/2019 | Weadock et al. |
| 2019/0150924 A1 | 5/2019 | Thompson et al. |
| 2019/0209173 A1 | 7/2019 | Thompson et al. |
| 2019/0209175 A1 | 7/2019 | Thompson et al. |
| 2019/0224029 A1 | 7/2019 | Thompson et al. |
| 2019/0261985 A1 | 8/2019 | Adams et al. |
| 2019/0261991 A1 | 8/2019 | Beckman et al. |
| 2019/0269408 A1 | 9/2019 | Jankowski |
| 2019/0274677 A1 | 9/2019 | Shelton, IV |
| 2019/0274678 A1 | 9/2019 | Shelton, IV |
| 2019/0274679 A1 | 9/2019 | Shelton, IV |
| 2019/0274680 A1 | 9/2019 | Shelton, IV |
| 2019/0307450 A1 | 10/2019 | Thompson et al. |
| 2019/0343519 A1 | 11/2019 | Thompson et al. |
| 2019/0380742 A1* | 12/2019 | Hall ............... A61B 17/0218 |
| 2019/0388092 A1 | 12/2019 | Thompson et al. |
| 2020/0008964 A1 | 1/2020 | Thompson et al. |
| 2020/0015822 A1 | 1/2020 | Marczyk et al. |
| 2020/0054326 A1 | 2/2020 | Harris et al. |
| 2020/0100790 A1 | 4/2020 | Dinardo et al. |
| 2020/0205810 A1 | 7/2020 | Posey et al. |
| 2020/0205827 A1 | 7/2020 | Bakos et al. |
| 2020/0206805 A1 | 7/2020 | Nalagatla et al. |
| 2020/0214703 A1 | 7/2020 | Thompson et al. |
| 2020/0229818 A1 | 7/2020 | Thompson et al. |
| 2020/0268385 A1 | 8/2020 | Dunki-Jacobs et al. |
| 2020/0297344 A1 | 9/2020 | Dunki-Jacobs et al. |
| 2020/0305865 A1 | 10/2020 | Shelton, IV |
| 2020/0305868 A1 | 10/2020 | Shelton, IV |
| 2020/0305869 A1 | 10/2020 | Shelton, IV |
| 2020/0305873 A1 | 10/2020 | Dunki-Jacobs et al. |
| 2020/0390443 A1 | 12/2020 | Thompson et al. |

(56) References Cited

U.S. PATENT DOCUMENTS

| | | | |
|---|---|---|---|
| 2021/0128335 | A1 | 5/2021 | Thompson et al. |
| 2021/0177411 | A1 | 6/2021 | Williams |
| 2021/0369330 | A1 | 12/2021 | Brandt et al. |
| 2021/0393319 | A1 | 12/2021 | Shelton, IV et al. |

FOREIGN PATENT DOCUMENTS

| | | | |
|---|---|---|---|
| EP | 399699 | A1 | 11/1990 |
| EP | 503662 | A1 | 9/1992 |
| EP | 666057 | A2 | 8/1995 |
| EP | 669104 | A1 | 8/1995 |
| EP | 1090592 | A1 | 4/2001 |
| EP | 1616526 | A1 | 1/2006 |
| EP | 1722691 | A1 | 11/2006 |
| EP | 1769766 | A1 | 4/2007 |
| EP | 1774916 | A1 | 4/2007 |
| EP | 1806101 | A1 | 7/2007 |
| EP | 1875868 | A1 | 1/2008 |
| EP | 1875870 | A1 | 1/2008 |
| EP | 1938759 | A2 | 7/2008 |
| EP | 2005896 | A2 | 12/2008 |
| EP | 2005897 | A2 | 12/2008 |
| EP | 2005898 | A2 | 12/2008 |
| EP | 2005899 | A2 | 12/2008 |
| EP | 2005900 | A2 | 12/2008 |
| EP | 2005901 | A1 | 12/2008 |
| EP | 2019633 | A1 | 2/2009 |
| EP | 2090247 | A1 | 8/2009 |
| EP | 2111803 | A2 | 10/2009 |
| EP | 2245993 | A2 | 11/2010 |
| EP | 2319424 | A1 | 5/2011 |
| EP | 2382928 | A1 | 11/2011 |
| FR | 2731895 | A1 | 9/1996 |
| GB | 2298905 | A | 9/1996 |
| WO | 0154594 | A1 | 8/2001 |
| WO | 2002060328 | A1 | 8/2002 |
| WO | 03094747 | A1 | 11/2003 |
| WO | 2007009099 | A2 | 1/2007 |
| WO | 2007019268 | A2 | 2/2007 |
| WO | 2007102152 | A2 | 9/2007 |
| WO | 2008039238 | A1 | 4/2008 |
| WO | 2008039249 | A1 | 4/2008 |
| WO | 2008039250 | A1 | 4/2008 |
| WO | 2008039270 | A1 | 4/2008 |
| WO | 2008042021 | A1 | 4/2008 |
| WO | 2008042022 | A1 | 4/2008 |
| WO | 2008042043 | A1 | 4/2008 |
| WO | 2008042044 | A2 | 4/2008 |
| WO | 2008042045 | A2 | 4/2008 |
| WO | 2008094210 | A1 | 8/2008 |
| WO | 2008141288 | A1 | 11/2008 |
| WO | 2009038550 | A1 | 3/2009 |
| WO | 2010011661 | A1 | 1/2010 |
| WO | 2011044032 | A2 | 4/2011 |
| WO | 2011094700 | A1 | 8/2011 |
| WO | 2012125615 | A2 | 9/2012 |
| WO | 2012141679 | A1 | 10/2012 |
| WO | 2013151888 | A1 | 10/2013 |
| WO | 2014026170 | A2 | 2/2014 |
| WO | 2014085099 | A1 | 6/2014 |
| WO | 2015063609 | A2 | 5/2015 |
| WO | 2015153324 | A1 | 10/2015 |
| WO | 2015153340 | A2 | 10/2015 |
| WO | 2016033221 | A1 | 3/2016 |

OTHER PUBLICATIONS

Parker, G.; A New Stomach Clamp; 26 Postgrad Med. J. 550; Oct. 1950; 1 page.
Harrah, J. D.; A Lung Clamp for Use with Mechanical Staplers; 28 The Annals of Thoracic Surgery 489; Nov. 1979; 2 pages.
Steichen, F. M. et al.; Stapling in Surgery; Figures 1-11C; Year Book Medical Publishers, Inc.; 1984; 3 pages.
Regan, J. P. et al.; Early Experience with Two-Stage Laparoscopic Roux-en-Y Gastric Bypass as an Alternative in the Super-Super Obese Patient; Obes Surg; 13(6):861-4; Dec. 1, 2003; abstract only; 2 pages.
AtriCure, Inc.; 510(k) Summary for AtriClip LAA Exclusion System with preloaded Gillinov-Cosgrove Clip; published Jun. 10, 2010; 6 pages.
Jacobs, M. et al.; Laparoscopic sleeve gastrectomy: a retrospective review of 1- and 2-year results; Surg Endosc. Apr. 2010; 24(4):781-5; doi: 10.1007/s00464-009-0619-8; Epub Aug. 19, 2009; abstract only; 2 pages.
LAAx, Inc.; 510(k) Summary for TigerPaw(R) System; published Oct. 29, 2010; 6 pages.
Zuckerman, B. D., Food and Drug Administration; Letter to AtriCure, Inc. Addressing Indication for Use of AtriClip LAA Exclusion System w/Pre-loaded Gillnov-Cosgrove Clip; Jun. 10, 2010; 3 pages.
Dept. of Health and Human Services; CMS Description of Open Left Atrial Appendage Occlusion with "U" Fastener Implant; Mar. 9, 2011; 1 page.
Pfiedler Enterprises; Science of Stapling: Urban Legend and Fact; Jun. 4, 2012; 38 pages.
Parikh, M. et al.; Surgical Strategies That May Decrease Leak After Laparoscopic Sleeve Gastrectomy; 257 Annals of Surgery 231; Feb. 2013; 7 pages.
International Search Report and Written Opinion of the International Searching Authority received in International Patent App. No. PCT/US2014/070869; mailed Apr. 21, 2015; 17 pages.
International Preliminary Report on Patentability and Written Opinion of the International Searching Authority received in International Patent App. No. PCT/US2015/048740; dated Mar. 7, 2017; 8 pages.
International Search Report and Written Opinion of the International Searching Authority received in International Patent App. No. PCT/US2015/022904; mailed Jun. 25, 2015; 6 pages.
International Search Report and Written Opinion of the International Searching Authority received in International Patent App. No. PCT/US2015/022990; mailed Sep. 30, 2015; 10 pages.
International Search Report and Written Opinion of the International Searching Authority received in International Patent App. No. PCT/US2015/048740; mailed Feb. 17, 2016; 12 pages.
European Search Report received in European Application No. 15774247; dated Dec. 23, 2016; 11 pages.
Supplementary Partial European Search Report received in European Application No. 14872137; dated Dec. 12, 2016; 5 pages.
Examination Report received in Australian Application No. 2016208416; dated May 18, 2017; 4 pages.
Supplementary European Search Report received in European Application No. 14872137; dated Mar. 28, 2017; 15 pages.
Supplementary European Search Report received in European Application No. 15772561; dated Mar. 15, 2017; 8 pages.
Examination Report received in Australian Application No. 2018203527; dated Oct. 22, 2018; 5 pages.
Examination Report received in European Application No. 15772561; dated Oct. 29, 2018; 7 pages.
International Preliminary Report on Patentability and Written Opinion of the International Searching Authority received in Application No. PCT/US2018/046743; dated Feb. 18, 2020; 17 pages.
International Search Report and Written Opinion of the International Searching Authority received in International Patent App. No. PCT/US2018/046743; mailed Dec. 4, 2018; 20 pages.
Search Report received in Chinese Application No. 201480075706.2; dated Nov. 28, 2018; 3 pages.
Examination Report received in Australian Application No. 2015241193; dated Dec. 11, 2018; 5 pages.
Examination Report received in Australian Application No. 2015241267; dated Feb. 25, 2019; 6 pages.
International Search Report and Written Opinion of the International Searching Authority received in International Patent Appln. No. PCT/US2022/021250; mailed Jun. 10, 2022; 12 pages.
Communication pursuant to Article 94(3) EPC received in European Patent Appln. No. 18 845 739.4; mailed Apr. 28, 2022; 9 pages.

(56) References Cited

OTHER PUBLICATIONS

Examination Report received in Australian Patent Appln. No. 2022204678; mailed Jul. 7, 2022; 4 pages.

* cited by examiner

SYSTEMS, DEVICES, AND METHODS FOR PREVENTING OR REDUCING LOSS OF INSUFFLATION DURING A LAPAROSCOPIC SURGICAL PROCEDURE

CROSS REFERENCE TO RELATED APPLICATIONS

This application claims priority to U.S. Provisional Patent Application No. 63/174,065, filed Apr. 13, 2021, and U.S. Provisional Patent Application No. 63/046,153, filed Jun. 30, 2020, each of which is hereby incorporated herein by reference in its entirety.

TECHNICAL FIELD

The examples herein may be directed to laparoscopic surgery, and more particularly, to a systems, devices, and methods for preventing or reducing loss of insufflation during laparoscopic surgical procedures involving the use of trocars and surgical instruments.

BACKGROUND

Obesity is a disease that affects a significant portion of the world's population and leads to multiple chronic medical conditions and premature death from cardiovascular events and cancer. In particular, the United States has a current, and worsening obesity epidemic. The U.S. Centers for Disease Control and Prevention (CDC) reports that over 33% of the US. population is obese, with a Body Mass Index (BMI) of over 30, and another 35-40% of the US population is overweight, with a BMI of 25-30. The CDC reports that the percent of the US population being either overweight or obese by 2018 will be 75%. The CDC also reports that obesity directly costs the U.S. economy $147 billion currently, and projects that the costs will approach $315 billion by 2020.

Further, obesity has environmental, genetic and behavioral origins but is intractable to most medical and behavioral interventions. To help reduce obesity and/or facilitate weight loss, bariatric surgery may be an option for some patients that may be overweight. Typically, bariatric surgery may be an effective long-term treatment option for patients with a BMI greater than 35. Despite the 20 million patients who are eligible for weight loss surgery in the U.S., the number of procedures per year has plateaued at about 200 thousand, eliminating any public health effect of surgery.

In recent years, a popular form of bariatric surgery may include a laparoscopic vertical sleeve gastrectomy (e.g., which may remove approximately 80% of the stomach). Laparoscopic vertical sleeve gastrectomy may be a procedure that may be safer and more effective for patients eligible for weight loss surgery. In fact, it has been accepted as the surgery that should be offered to most morbidly obese patients over, for example, laparoscopic adjustable gastric banding and laparoscopic Roux-en-Y gastric bypass. As such, the surgery has been adopted by bariatric surgeons and is now the most commonly performed weight loss surgery.

Vertical sleeve gastrectomy is typically performed using standard laparoscopic or "minimally invasive" equipment. Laparoscopic surgical techniques are typically performed using a device known as a trocar or cannula, which facilitates the introduction of laparoscopic instruments into, for example, the abdominal (peritoneal) cavity of a patient. Such procedures commonly involve filling or "insufflating" the abdominal cavity with a pressurized fluid, such as carbon dioxide, to create adequate workspace between the viscera and abdominal wall. If insufflation is not properly maintained during laparoscopic surgery, the surgeon's view of the surgical area may be obstructed.

Introduction of surgical instruments into the inflated abdominal cavity without a substantial loss of insufflation gas is desirable. Such surgical instruments can include, for example, staplers, grasping instruments, cauterizing units, light sources, cameras, among other instruments. A trocar must maintain the pressure within the cavity by sealing between the trocar and the surgical instrument being used, while still allowing the surgeon to manipulate the surgical instruments. Trocars are designed to maintain a seal before the insertion of an instrument and after the removal of the instrument. As a result, many trocars provide double sealing systems. A double sealing system can include a top or proximal seal (e.g., a lip seal) used to seal around the instrument when inserted therethrough and a duckbill seal provided below the top seal for sealing the trocar housing when the instrument is not present.

Even with a double sealing system, it is expected to have some insufflation loss while the instrument is being inserted. For example, where an instrument includes an end effector extending from a sealed shaft, the end effector may not be sealed such that gas can leak out of the trocar while the end effector is passing through the seal(s). Thus, insufflation may be lost in the time between inserting the end effector and the shaft reaching the sealing system. As a result, a need currently exists for an improved trocar assembly that reduces or prevents insufflation loss while an instrument is being inserted through the trocar.

SUMMARY

The following provides a summary of certain example implementations of the disclosed inventive subject matter. This summary is not an extensive overview and is not intended to identify key or critical aspects or elements of the disclosed inventive subject matter or to delineate its scope. However, it is to be understood that the use of indefinite articles in the language used to describe and claim the disclosed inventive subject matter is not intended in any way to limit the described inventive subject matter. Rather the use of "a" or "an" should be interpreted to mean "at least one" or "one or more".

One implementation of the disclosed technology provides a system for reducing insufflation loss due to gas leakage during a laparoscopic surgical procedure, comprising a trocar through which a surgical stapling instrument having a stapler portion is inserted for access to the abdominal cavity of a patient receiving laparoscopic surgery, wherein the trocar comprises: a lip; a lip seal disposed within the lip; a cannula located beneath the lip, wherein the cannula includes an upper portion and a lower portion; a sealing valve disposed within the upper portion of the cannula; and a sealing device disposed within the lower portion of the cannula. The sealing device may include a balloon disposed within the lower portion of the cannula, wherein the balloon is attached to a balloon pump tube that is operative to inflate or deflate the balloon.

Another implementation of the disclosed technology provides a system for reducing insufflation loss due to gas leakage during a laparoscopic surgical procedure, comprising a trocar through which a surgical stapling instrument having a stapler portion is inserted for access to the abdominal cavity of a patient receiving laparoscopic surgery, wherein the trocar comprises a lip; a lip seal disposed within the lip; a cannula located beneath the lip, wherein the cannula includes an upper portion and a lower portion; and a diametrically expanding valve disposed within the lower portion of the cannula. The diametrically expanding valve may be a cross-slit valve, dilating valve, or trap door valve.

Another implementation of the disclosed technology provides system for reducing insufflation loss due to gas leakage during a laparoscopic surgical procedure, comprising a trocar through which a surgical stapling instrument having a stapler portion is inserted for access to the abdominal cavity of a patient receiving laparoscopic surgery, wherein the trocar comprises a lip; a lip seal disposed within the lip; a cannula located beneath the lip, wherein the cannula includes an upper portion and a lower portion; a sealing valve disposed within the upper portion of the cannula; and a sealing device, wherein the sealing device is integrated into the distal end of the stapling instrument. The sealing device may include a tip attached to an end of the stapler portion and a lip seal mounted on the tip, wherein the lip seal mounted on the tip cooperates with the lower portion of the cannula to form a seal.

Another implementation of the disclosed technology provides a system for reducing insufflation loss due to gas leakage during a laparoscopic surgical procedure, comprising a trocar through which a surgical stapling instrument having a stapler portion is inserted for access to the abdominal cavity of a patient receiving laparoscopic surgery, wherein the trocar comprises a lip; a lip seal disposed within the lip; a cannula located beneath the lip; a sealing valve disposed within the cannula; and a sealing device configured as an accessory to the trocar.

The sealing device may mount on the stapling instrument and include a hub, a retaining ring disposed within the hub, a lip seal disposed within the retaining ring, and a rigid sheath attached to the hub for covering the stapler portion of the stapling instrument. The sealing device may mount on the stapling instrument and include a hub, a retaining ring disposed within the hub, a lip seal disposed within the retaining ring, a plurality of bristles mounted in a circular pattern behind the retaining ring, and a telescoping sleeve attached to the hub for covering the stapler portion of the stapling instrument. The sealing device may mount on the stapling instrument and include a hub, a retaining ring disposed within the hub, a lip seal disposed within the retaining ring, and an unrolling sleeve attached to the hub for covering the stapler portion of the stapling instrument, wherein the sleeve includes an aperture formed in the tip thereof. The sealing device may mount on the stapling instrument and include a proximal hub, a lip seal disposed within the proximal hub, a flexible and collapsible sleeve attached to the proximal hub, and a trocar mating hub attached to the sleeve.

Another implementation of the disclosed technology provides a method for reducing insufflation loss due to gas leakage during a laparoscopic surgical procedure, wherein the surgical procedure includes the use of a stapling instrument having a stapler portion; and a trocar through which the stapling instrument is inserted for access to the abdominal cavity of a patient receiving laparoscopic surgery, the trocar comprising a lip, a lip seal disposed within the lip, and a cannula located beneath the lip, the method comprising providing a sealing device, wherein the sealing device is disposed within the cannula of the trocar, configured as an accessory to the trocar, or integrated into the stapling instrument.

The sealing device may be disposed within the cannula of the trocar and include a diametrically expanding valve. The diametrically expanding valve may be a cross-slit valve, dilating valve, or trap door valve.

The method may further comprising providing a sealing valve disposed within the cannula. The sealing device may be disposed within the cannula of the trocar and include a balloon, wherein the balloon is attached to a balloon pump tube that is operative to inflate or deflate the balloon. The sealing device may be integrated into the stapling instrument and include a blunt tip attached to an end of the stapler portion and a lip seal mounted on the blunt tip, wherein the lip seal mounted on the blunt tip cooperates with the lower portion of the cannula to form a seal. The sealing device may be configured as an accessory to the trocar that mounts on the stapling instrument and includes a hub, a retaining ring disposed within the hub, a lip seal disposed within the retaining ring, and a rigid sheath attached to the hub for covering the stapler portion of the stapling instrument. The sealing device may be configured as an accessory to the trocar that mounts on the stapling instrument and that includes a hub, a retaining ring disposed within the hub, a lip seal disposed within the retaining ring, a plurality of bristles mounted in a circular pattern behind the retaining ring, and a telescoping sleeve attached to the hub for covering the stapler portion of the stapling instrument. The sealing device may be configured as an accessory to the trocar that mounts on the stapling instrument and that includes a hub, a retaining ring disposed within the hub, a lip seal disposed within the retaining ring, and an unrolling sleeve attached to the hub for covering the stapler portion of the stapling instrument, wherein the sleeve include an aperture formed in the tip thereof. The sealing device may be configured as an accessory to the trocar that mounts on the stapling instrument and that includes a proximal hub, a lip seal disposed within the proximal hub, a flexible and collapsible sleeve attached to the proximal hub, and a trocar mating hub attached to the sleeve.

It should be appreciated that all combinations of the foregoing concepts and additional concepts discussed in greater detail below (provided such concepts are not mutually inconsistent) are contemplated as being part of the inventive subject matter disclosed herein and may be implemented to achieve the benefits as described herein. Additional features and aspects of the disclosed system, devices, and methods will become apparent to those of ordinary skill in the art upon reading and understanding the following detailed description of the example implementations. As will be appreciated by the skilled artisan, further implementations are possible without departing from the scope and spirit of what is disclosed herein. Accordingly, the drawings and associated descriptions are to be regarded as illustrative and not restrictive in nature.

BRIEF DESCRIPTION OF THE DRAWINGS

The present disclosure will be more readily understood from a detailed description of some example embodiments taken in conjunction with the following figures.

DETAILED DESCRIPTION

Figure 1:
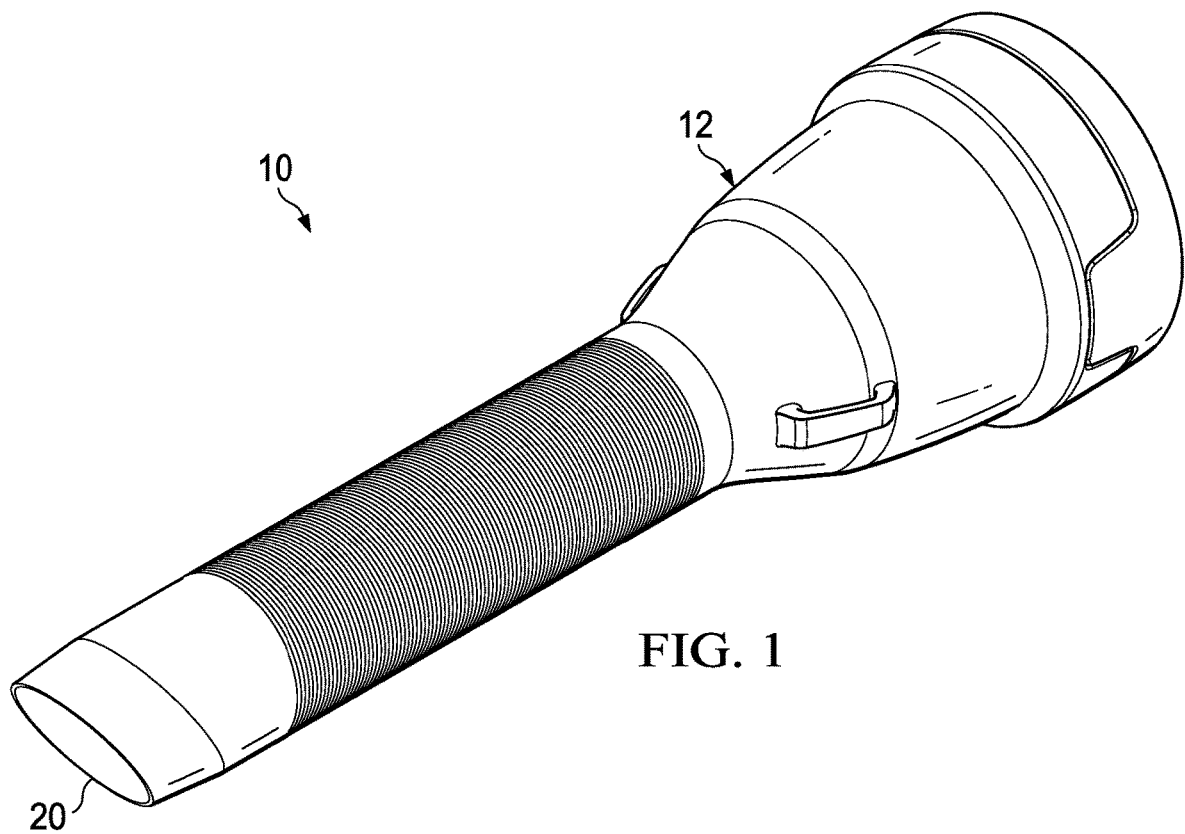
FIG. 1 is a perspective view of a trocar assembly according to an embodiment showing the trocar.
Figure 2:
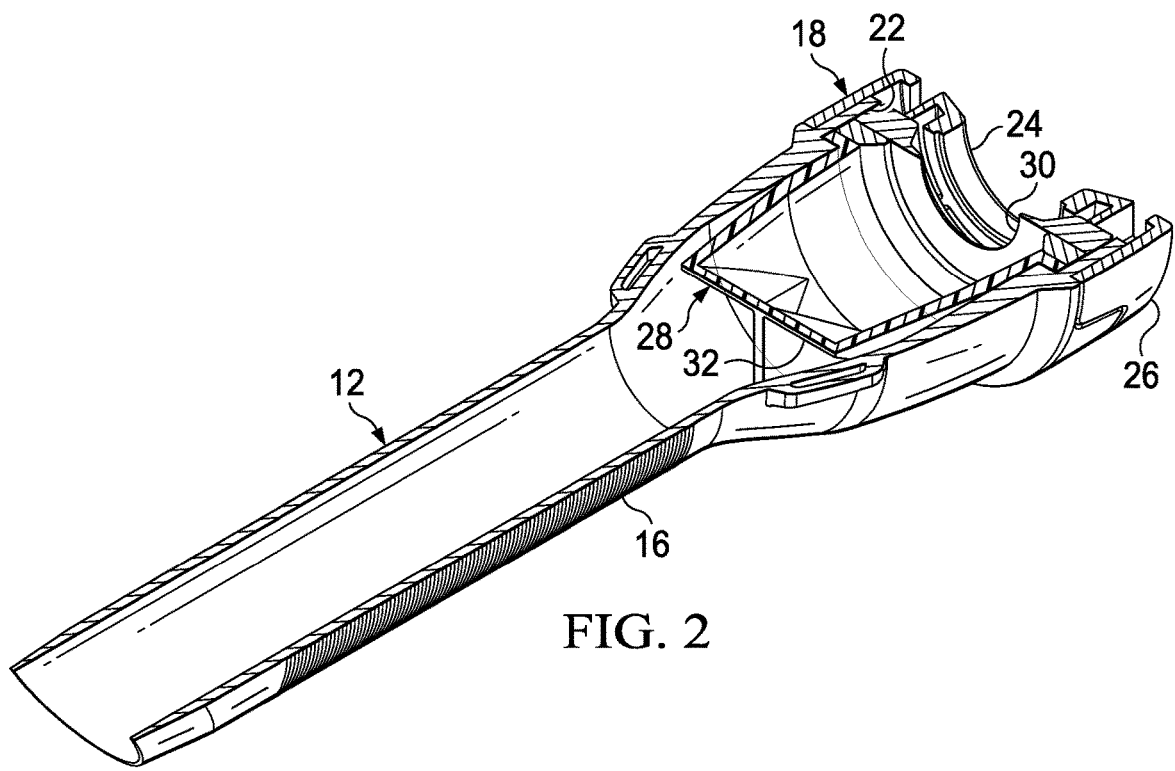
FIG. 2 is a cross-sectional view of the trocar of FIG. 1.

Various non-limiting embodiments of the present disclosure will now be described to provide an overall understanding of the principles of the structure, function, and use of the devices, systems, methods, and processes disclosed herein. One or more examples of these non-limiting embodiments are illustrated in the accompanying drawings. Those of ordinary skill in the art will understand that systems and methods specifically described herein and illustrated in the accompanying drawings are non-limiting embodiments. The features illustrated or described in connection with one non-limiting embodiment may be combined with the features of other non-limiting embodiments. Such modifications and variations are intended to be included within the scope of the present disclosure.

Reference throughout the specification to "various embodiments," "some embodiments," "one embodiment," "some example embodiments," "one example embodiment," or "an embodiment" means that a particular feature, structure, or characteristic described in connection with any embodiment is included in at least one embodiment. Thus, appearances of the phrases "in various embodiments," "in some embodiments," "in one embodiment," "some example embodiments," "one example embodiment," or "in an embodiment" in places throughout the specification are not necessarily all referring to the same embodiment. Furthermore, the particular features, structures or characteristics may be combined in any suitable manner in one or more embodiments.

Trocars or abdominal access systems are available in sizes ranging from 3 mm to 12 mm (and above) and are typically divided into two main categories: cutting trocars and dilating trocars. Cutting trocars include a sharp metal or plastic blade that cuts through the various tissue layers as pressure is applied, thereby permitting easy insertion into the abdominal category. Dilating trocars include a blunt tip that separates and dilates tissue under pressure. Dilating trocars are noncutting instruments and eliminate the blade used in cutting systems for minimizing the risk of cutting internal organs.

Regardless of type, trocars typically include three main sections or components, a cannula, a lip seal, a cross-slit or intermediate check vale, and an obturator which may include a metal or plastic sharpened or non-bladed tip. The cannula is essentially a hollow tube that extends between the lip seal and the tip of the device. The lip seal is located at the top of the cannula and is intended to prevent air from escaping from the abdominal cavity while still permitting any necessary devices or equipment to be passed through the seal into the cannula. The obturator (also referred to as an awl) is located at the bottom of the cannula opposite the seal and enables the cannula to make the initial penetration into the abdomen. In addition to the lip seal, a trocar may include a one-way access valve located beneath the lip seal that permits an instrument such as a catheter or camera to open the valve when inserted into valve, but that closes upon removal of the instrument. This type of access valve may be referred to as a cross-slit valve, a duckbill valve, a flap valve, or a dome valve. A lip seal and a cross-slit valve cooperate to maintain insufflation pressure during laparoscopic surgical procedures. The lip seal maintains insufflation pressures after the shaft of a medical instrument has advanced past the seal and during device use in the surgical space. The cross-slit valve maintains insufflation when no device is present in the trocar.

Laparoscopic surgical devices having long end effectors can create leak paths in existing trocars, thereby resulting in the loss of adequate insufflation. A leak path is created when the two seals in existing trocars (e.g., the lip seal and the cross-slit valve) are both penetrated by the end portion of the laparoscopic surgical device. This leak path exists until the shaft of the surgical device reaches the lip seal which then seals around the shaft. This problem has been recognized with existing 45 mm and 60 mm stapler devices having jaws that are long enough to penetrate both seals prior to reaching the shaft of the stapling instrument. Accordingly, an accessory or device design that prevents or at least reduces air leakage during surgical device insertion past the lip seal and cross-slit valve of a trocar would be highly beneficial.

The examples discussed herein are examples only and are provided to assist in the explanation of the apparatuses, devices, systems and methods described herein. None of the features or components shown in the drawings or discussed below should be taken as mandatory for any specific implementation of any of these the apparatuses, devices, systems or methods unless specifically designated as mandatory. For ease of reading and clarity, certain components or methods may be described solely in connection with a specific figure. Any failure to specifically describe a combination or subcombination of components should not be understood as an indication that any combination or sub-combination is not possible. Also, for any methods described, it should be understood that unless otherwise specified or required by context, any explicit or implicit ordering of steps performed in the execution of a method does not imply that those steps must be performed in the order presented but instead may be performed in a different order or in parallel.

Example embodiments described herein can reduce the loss of insufflation when inserting an instrument through a trocar. Instruments can have an unsealed portion (e.g., end effector, such as a stapler) and a sealed portion (e.g., shaft). If the instrument being inserted has a relatively long end effector (e.g., 250 mm compared to 45 mm to 60 mm), the expected loss of insufflation when inserting the end effector through a conventional trocar could be significant. Example lengths of unsealed portions of the instrument (e.g., end effector) can be in a range of, without limitation, 60 mm to 300 mm, 65 mm to 300 mm, 100 mm to 300 mm, 100 mm to 250 mm, or 200 mm to 300 mm. Example lengths of unsealed portions of the instrument can also be greater than 60 mm or greater than 100 mm. Further, such a relatively long end effector could exit the trocar before the shaft reaches the seal(s). A substantial loss of insufflation could result in loss of visualization and, if the end effector has already exited the trocar, potential injury to the patient from inadvertent contact with patient anatomy due to the lack of visualization.

Described herein are example embodiments of apparatuses, systems, and methods for reducing insufflation loss when inserting an instrument through a trocar. In one example embodiment, a trocar assembly includes a trocar and a trocar sheath. In some embodiments, the instrument is first inserted through the trocar sheath, and the instrument and trocar sheath are then inserted together through the trocar. The trocar sheath can reduce the loss of insufflation compared to a system without the trocar sheath.

With reference to FIGS. 1-11, according to an embodiment, a trocar assembly 10 may include a trocar 12 and an obturator 14. As shown in FIG. 1, the trocar 12 can include a trocar cannula 16 and a trocar housing 18. The trocar cannula 16 defines an interior lumen (see FIG. 2) having an open distal end 20 and an open proximal end 22. The proximal end 22 extends into and is coupled to the trocar housing 18. The distal end 20 of the trocar cannula 16 can be beveled. The trocar housing 18 has an open proximal end portion that defines an opening 24. The trocar housing 18 includes cannula cap 26 and a trocar seal assembly 28. In an embodiment, the trocar seal assembly 28 includes a first seal 30 proximate the opening 24 of the trocar housing 18 and a second seal 32 distal of the first seal 30 within the trocar housing 18. In an embodiment, the first seal 30 can be a lip seal, and the second seal 32 can be a cross-slit valve or duckbill valve, such as a double duckbill valve. It will be appreciated that the trocar seal assembly can include one seal or more than two seals and have a variety of configurations. It will be recognized that the trocar seal assembly 28 cooperates with the obturator 14 or another surgical instrument extending through the trocar cannula 16 to sealingly engage the outer surface thereof and thereby preclude the passage of fluids through the trocar 12.

Figure 3:
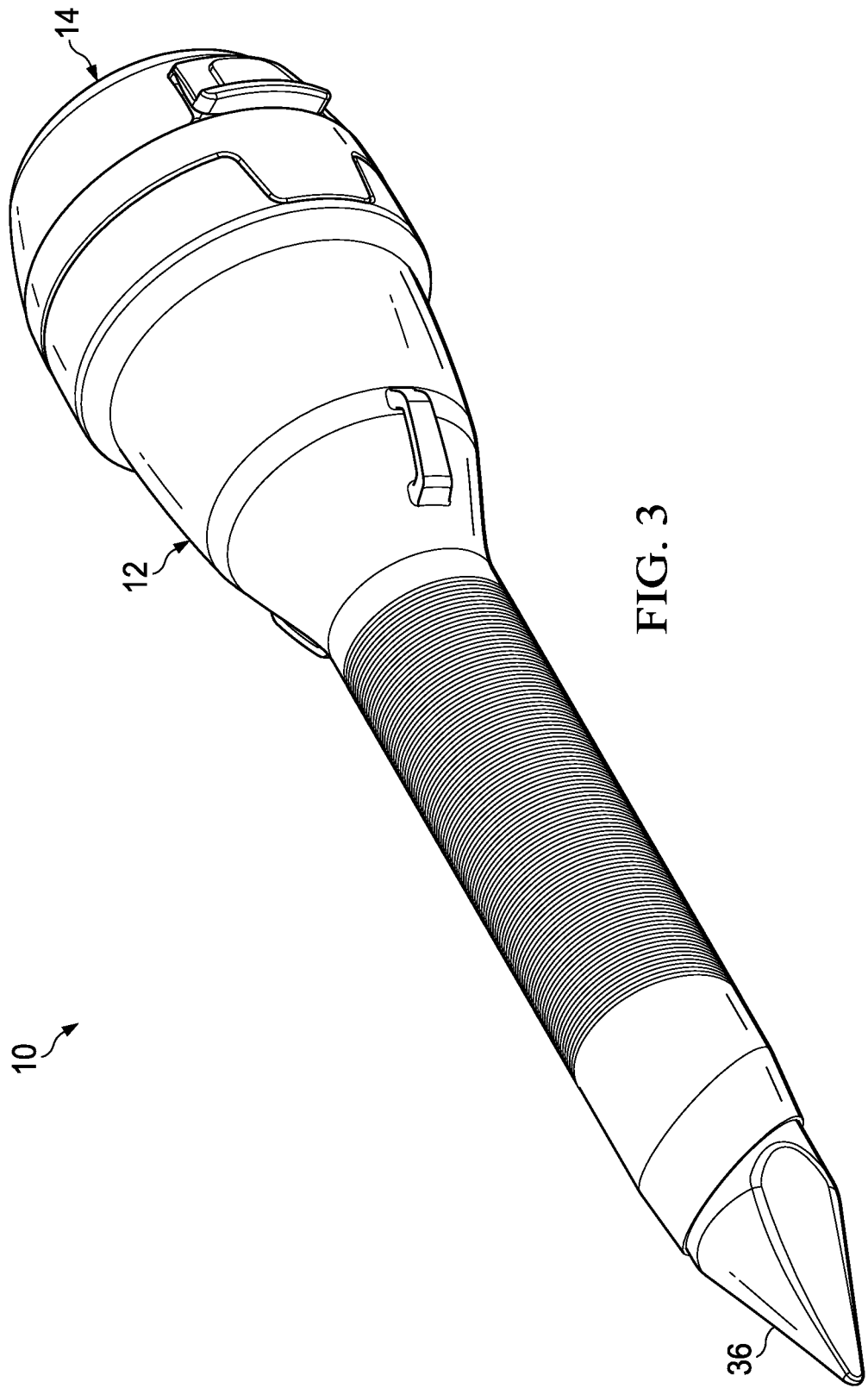
FIG. 3 is a perspective view of the trocar assembly showing the trocar of FIG. 1 and an obturator.
Figure 4:
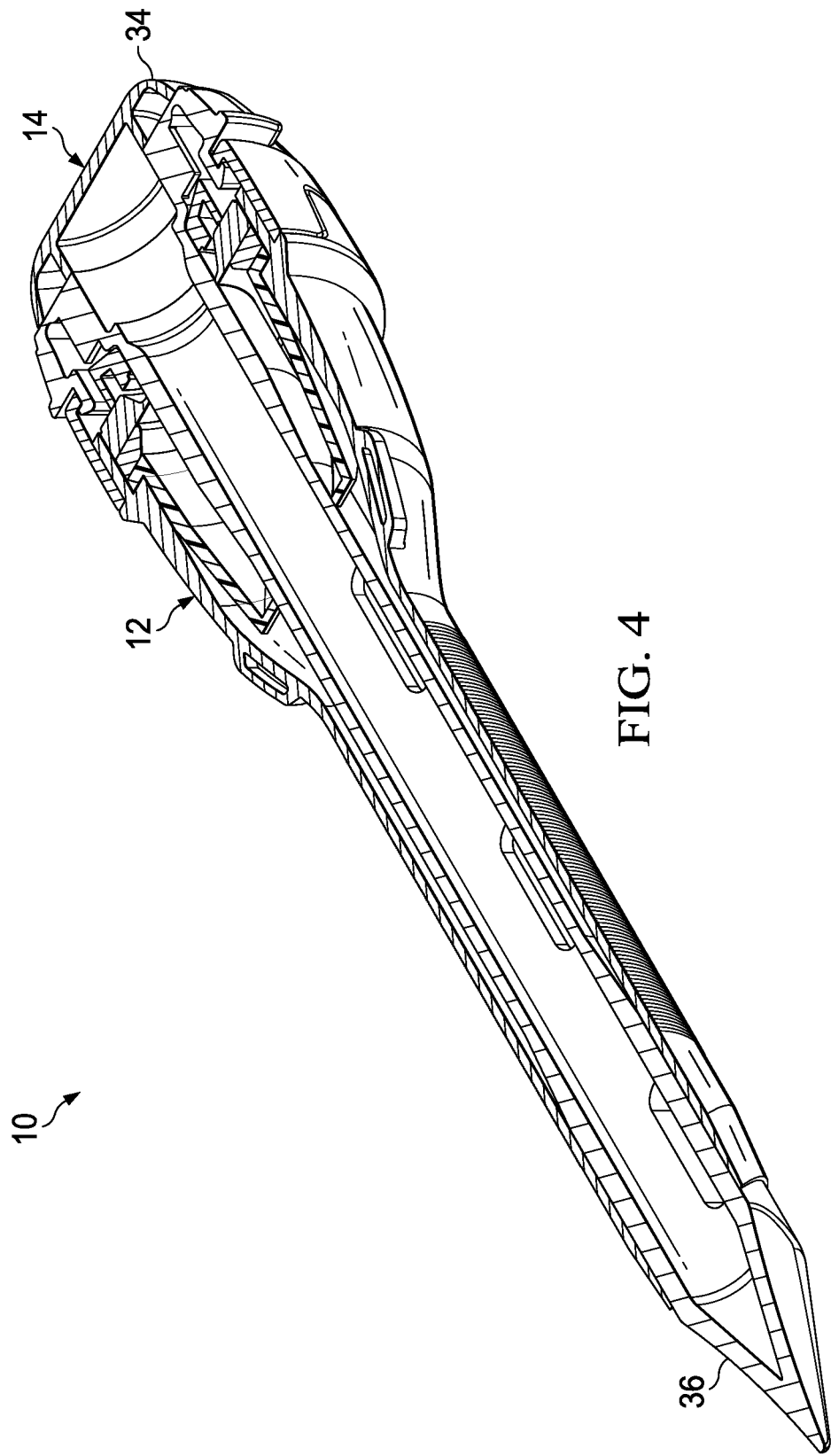
FIG. 4 is a cross-sectional view of the trocar of FIG. 1 and the obturator of FIG. 3.

With reference to FIGS. 3 and 4, the obturator 14 is slidably and removably extendable within the trocar 12. The obturator 14 can be removably inserted into the opening 24 of the trocar housing 18, through the trocar seal assembly 28, through the trocar cannula 16 and out of the distal end 20 of the trocar cannula 16. An obturator handle 34 is provided at the proximal end of the obturator 14 and a sharpened point or blade 36 is formed at the distal end thereof. When inserted in the trocar 12, the obturator handle 34 abuts the trocar housing 18, and the blade 36 of the obturator 14 extends out of the distal end 20 of the trocar cannula 16. The trocar 12 and obturator 14 are used together to puncture a hole in soft tissue by placing the blade 36 of the obturator 14 against the tissue and pressing against the obturator handle 34. After the blade 36 breaks through the inner surface of the tissue, the obturator 14 can be removed, and the trocar 12 creates an open passageway through the tissue.

Figure 5:
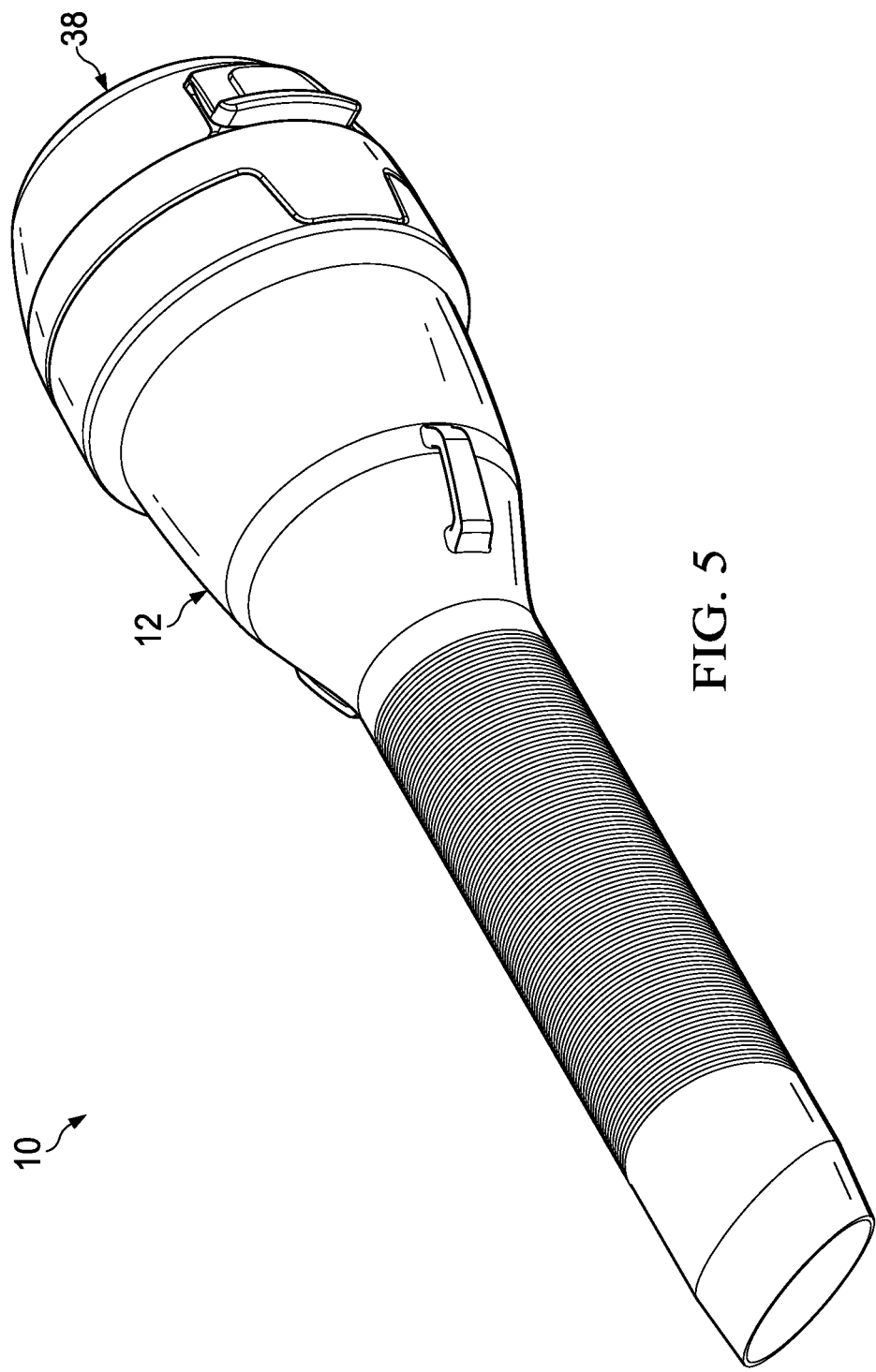
FIG. 5 is a perspective view of the trocar assembly showing the trocar of FIG. 1 and an adaptor.
Figure 6:
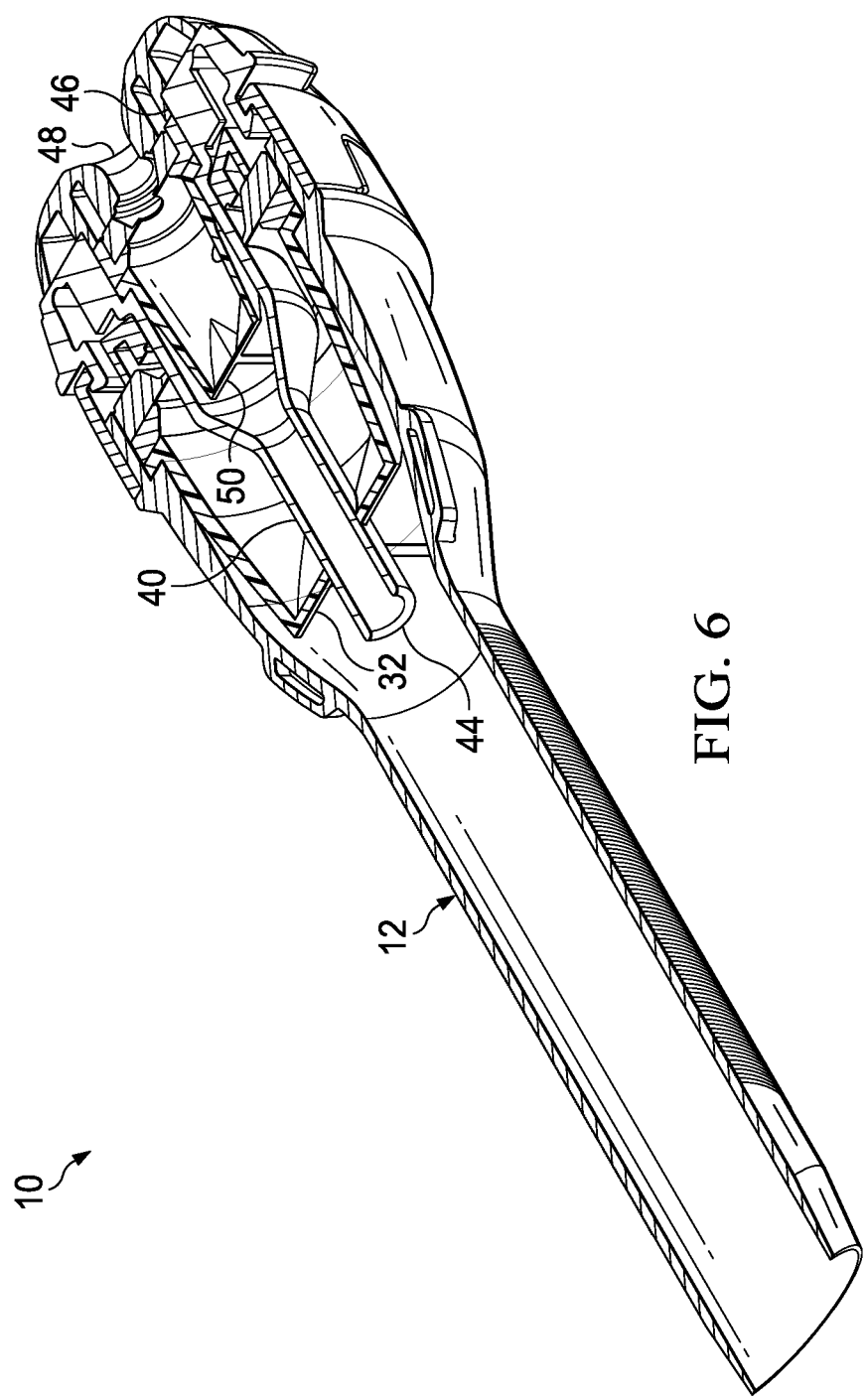
FIG. 6 is a cross-sectional view of the trocar of FIG. 1 and adaptor of FIG. 5.
Figure 7:
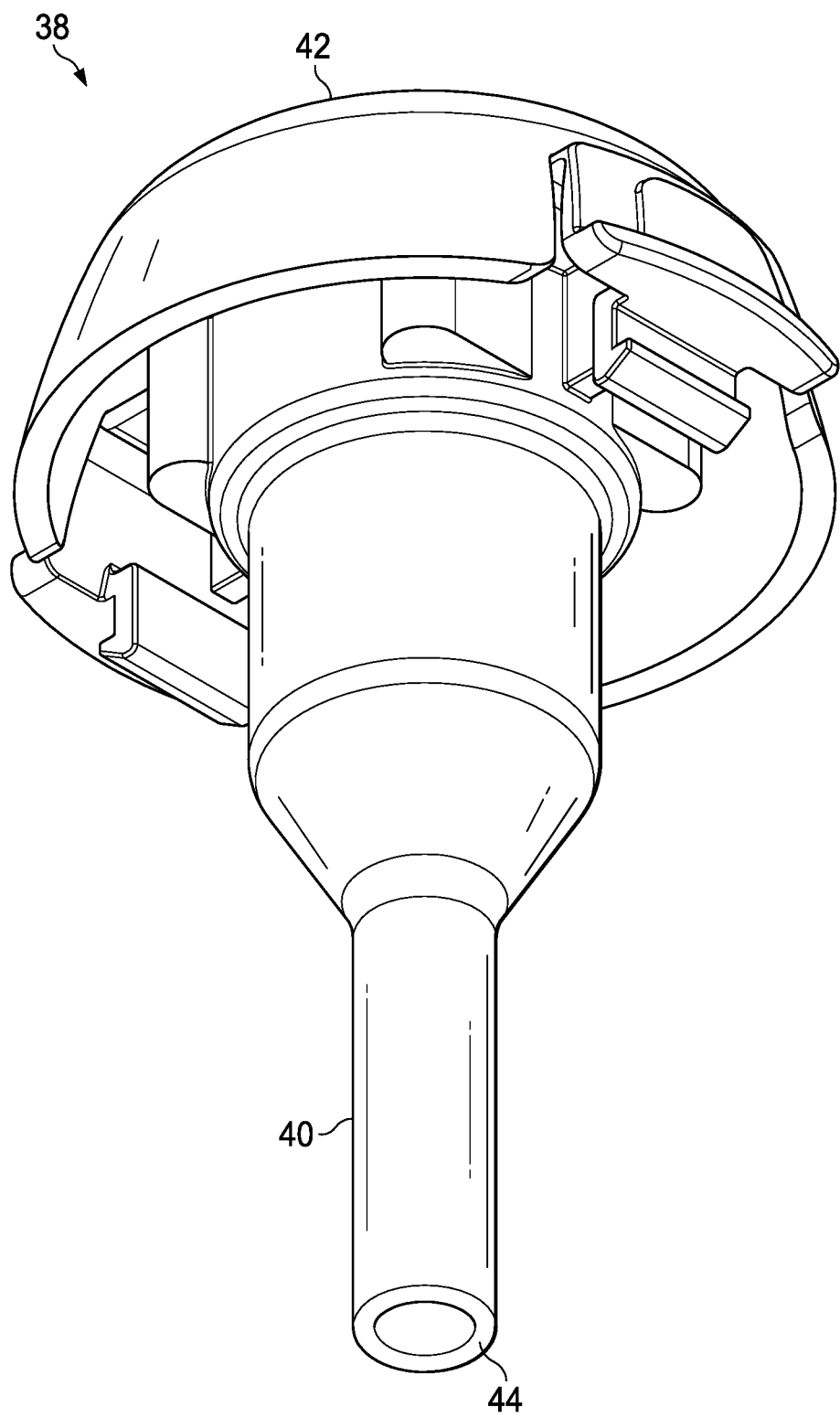
FIG. 7 is a bottom perspective view of the adaptor of FIG. 5.

Referring now to FIGS. 5-7, in an embodiment, the trocar assembly 10 can include an adapter 38. As will be understood, the trocar 12 can be generally sized to fit instruments or tools in a particular size range. When an instrument that is significantly smaller than that size is inserted into the trocar 12, the trocar seal assembly 28 will not provide a proper seal. As shown in FIG. 5, the adapter 38 can be inserted in the opening 24 of the trocar housing 18 to allow for smaller instruments to be used with the trocar 12 while providing a proper seal. The adapter 38 includes an adapter cannula 40 extending from an adapter housing 42. The adapter cannula 40 defines an interior lumen having an open distal end 44 and an open proximal end 46. The proximal end 46 extends into and is coupled to the adapter housing 42. The adapter housing 42 has an open proximal end portion that defines an opening 48. As shown in FIG. 6, when inserted in the trocar 12, the adapter housing 42 abuts the trocar housing 18, and the distal end 44 of the adapter cannula 40 extends into and is fluidically coupled with the trocar cannula 16. The opening 48 of the adapter 38 is smaller than the opening 24 of the trocar housing 18. The adapter 38 can also include an adapter seal assembly 50. In an embodiment, the adapter seal assembly 50 can include a first seal proximate the opening 48 of the adapter housing 42 and a second seal distal of the first seal within the adapter housing 42. In an embodiment, the first seal can be a lip seal, and the second seal can be a cross-slit valve or duckbill valve, such as a double duckbill valve. It will be appreciated that the adapter seal assembly can include one seal or more than two seals and have a variety of configurations. It will be recognized that the adapter seal assembly 50 cooperates with a surgical instrument extending through the adapter cannula 40 to sealingly engage the outer surface thereof and thereby preclude the passage of fluids through the trocar 12 and the adapter 38.

As shown in FIGS. 8-11, in an embodiment, the trocar assembly 10 can include a trocar sheath 52. The trocar sheath 52 is slidably and removably extendable within the trocar 12. The trocar sheath 52 can be removably inserted into the opening 24 of the trocar housing 18, through the trocar seal assembly 28, and through the trocar cannula 16. The trocar sheath 52 can include a sheath cannula 54 and a housing assembly 56. The sheath cannula 54 defines an interior lumen having an open distal end 58 and an open proximal end 60. The proximal end 60 extends into and is coupled to the housing assembly 56. The housing assembly 56 has an open proximal end portion that defines an opening 62. In some embodiments, the sheath cannula 54 is a thin-walled tube made from plastic, such as HDPE, that is rigid enough to not collapse during use while thin enough to not increase the required inner diameter of the trocar 12 significantly. In another embodiment, the sheath cannula 54 can be flexible. The wall thickness of the sheath cannula 54 can be in a range of, for example, 0.005 inches to 0.01 inches, such as 0.008 inches. The sheath cannula 54 can be transparent, semi-transparent, translucent, or opaque in various embodiments. While the trocar sheath 52 is shown as being a separate component from the trocar 12, in other embodiments, the trocar 12 and trocar sheath 52 may be co-molded or co-formed.

Figures 8, 9:
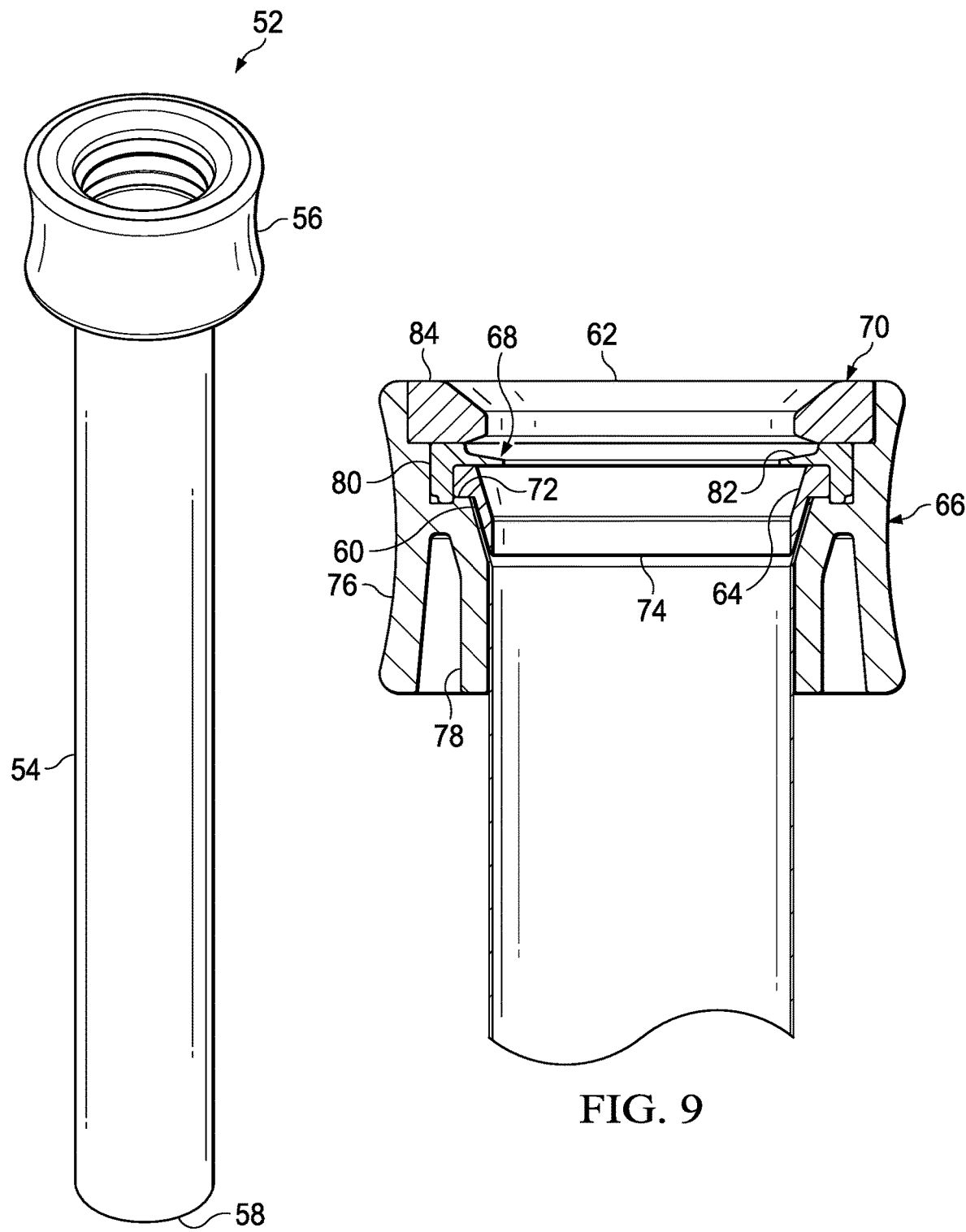
FIG. 8 is a top perspective view of a trocar sheath according to an embodiment.
FIG. 9 is a partial cross-sectional view of the trocar sheath of FIG. 8.
Figure 11:
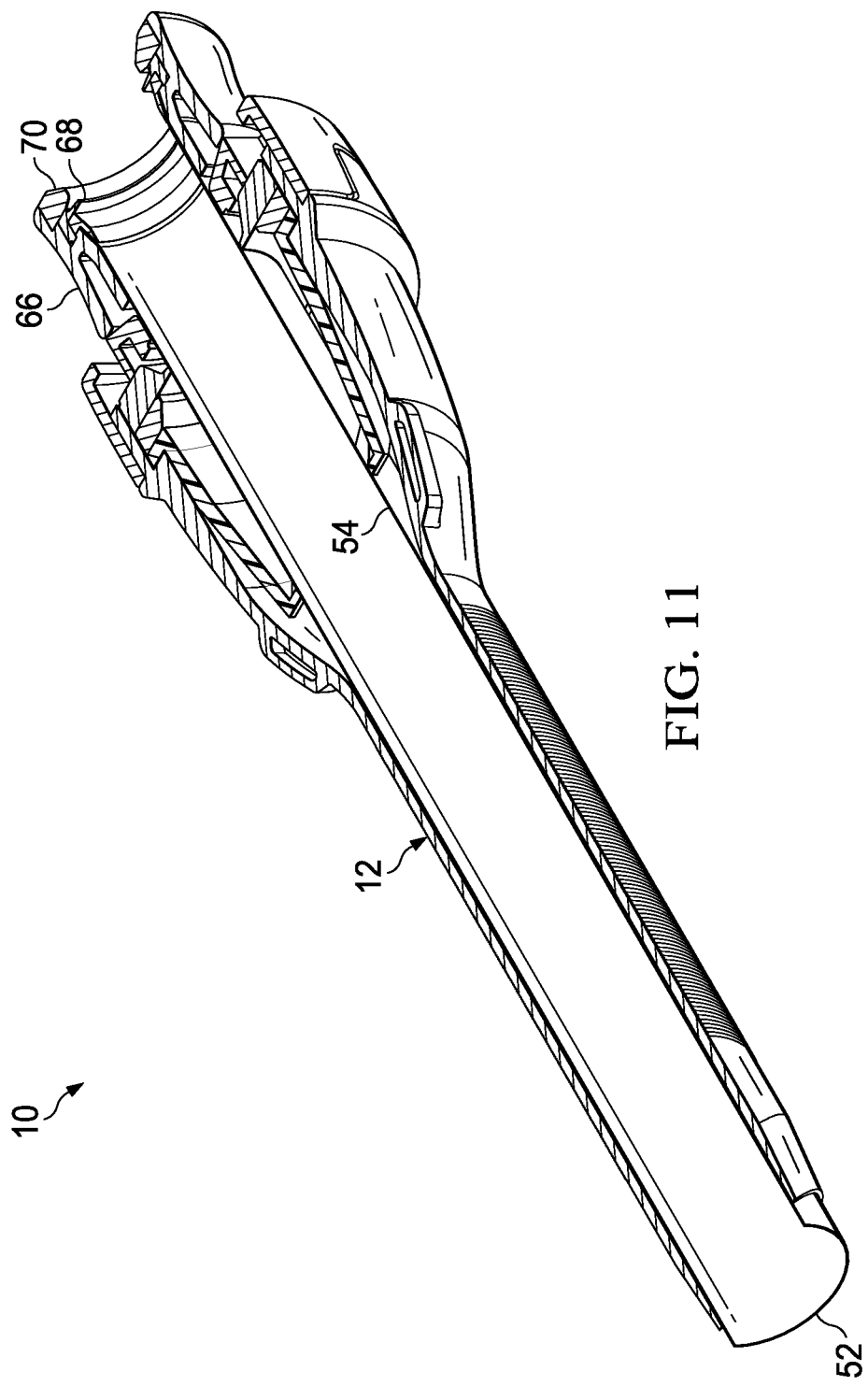
FIG. 11 is a cross-sectional view of the trocar and trocar sheath of FIG. 10.

With further reference to FIGS. 9 and 11, in an embodiment, the housing assembly 56 can include a seal plate 64, a sheath hub 66, a sheath seal 68, and a sheath cap 70. The seal plate 64 may be coupled to the proximal end 60 of the sheath cannula 54. The seal plate 64 defines an opening and includes a proximal lip 72 extending from a distal skirt 74. The skirt 74 can be sized to extend into the open proximal end 60 of the sheath cannula 54. The sheath hub 66 is coupled to an exterior of the proximal end 60 of the sheath cannula 54. The proximal end 60 of the sheath cannula 54 that is captured in the sheath hub 66 can be outwardly flared to provide a mechanical locking feature without reducing the effective inner diameter of the sheath cannula 54. The seal plate 64 can be correspondingly flared. The seal plate 64 captures the sheath cannula 54 to withstand tensile loading during use.

Still referring to FIGS. 9 and 11, in an embodiment, the sheath hub 66 can include an outer wall 76 defining an opening therethrough. The outer wall can be, for example, concave and act as a grip. The sheath hub 66 can also in include an inner skirt 78 extending from the outer wall 76 towards a distal end of the sheath hub 66. Thus, the diameter of the sheath hub 66 may vary. For example, the diameter of the opening at the proximal end of the sheath hub 66 at the outer wall 76 can be larger than the diameter of the opening at the distal end of the sheath hub 66 at the inner skirt 78. It will be recognized that the configuration of the sheath hub 66 may vary. For example, the sheath hub 66 may have a single skirt wall. The sheath seal 68 and the sheath cap 70 are sized to fit in the opening of the sheath hub 66. The sheath seal 68 and the sheath cap 70 may be contained by the sheath hub 66. The sheath seal 68 includes a generally circular outer wall 80 defining an opening. In an example configuration, the sheath seal 68 is a lip seal and includes a lip 82 extending into the opening from the outer wall 80. The sheath seal 68 can be configured to have less drag relative to the shaft of the instrument inserted therethrough versus the drag between the trocar seal assembly 28 and the trocar sheath 52. In an embodiment, the drag on an instrument while it is being inserted through the sheath seal 68 may be less than the drag on the instrument while removing it through the sheath seal 68. The sheath cap 70 also includes a generally circular outer wall 84 defining an opening. The sheath cap 70 can provide, in some embodiments, axial preload on the proximal end 60 of the sheath cannula 54, the sheath seal 68, and the seal plate 64 contained in the sheath hub 66 to provide a hermetic seal to prevent air leakage in use. In various embodiments, the sheath cap 70 can be held in place using an ultrasonic welding process, glue, or a snap fit.

In an embodiment, the trocar sheath 52 may include a housing assembly 56 without a seal. The difference between the inner diameter of the sheath cannula 54 and the outer diameter of the instrument may be very small. For example, the difference between the inner diameter of the sheath cannula 54 and the outer diameter of the instrument can be in a range of 0.001 inches to 0.01 inches, 0.001 inches to 0.005 inches, 0.005 inches to 0.01 inches, or 0.002 inches to 0.005 inches.

Figure 10:
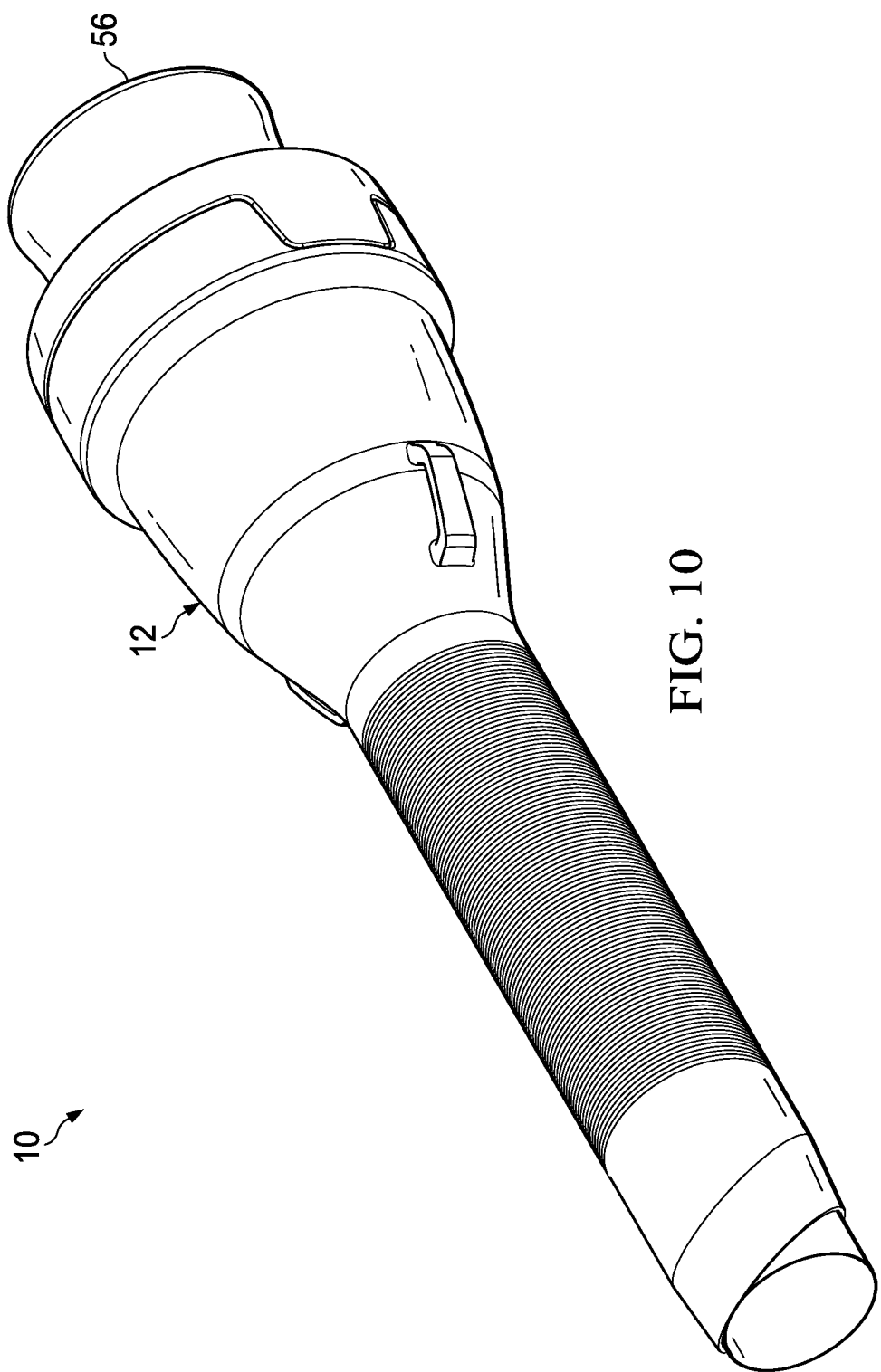
FIG. 10 is a perspective view of the trocar assembly showing the trocar of FIG. 1 and the trocar sheath of FIG. 8.

FIGS. 10 and 11 depict the trocar sheath 52 positioned in the trocar 12. As shown, the sheath cannula 54 can extend beyond the distal end 20 of the trocar cannula 16. In another embodiment, the sheath cannula 54 is sized to extend no further than the beveled end of distal end 20 of the trocar cannula 16. In other words, in such a configuration, a portion of the sheath cannula 54 can be uncovered by the trocar cannula due to the beveling, but the beveled end of the trocar cannula 16 extends past the distal end 58 of the sheath cannula 54. When the trocar sheath 52 is positioned in the trocar 12, the trocar seal assembly 28 cooperates with trocar sheath 52 to sealingly engage the outer surface thereof. Similarly, when an instrument is positioned in the trocar sheath 52, the housing assembly 56 of the trocar sheath 52 cooperates with the instrument to sealingly engage the outer surface thereof. Thus, in a configuration, the trocar 12, the trocar sheath 52, and an instrument inserted through the trocar sheath 52 cooperate to preclude the passage of fluids through the trocar 12.

In various embodiments, the trocar sheath 52 can include a locking feature on (e.g., on the sheath hub 66) to lock the proximal end of the instrument shaft (e.g., the handle of a stapler) to the trocar sheath 52. Example configurations include a quick-connect fitting, radial compression spring that locks onto the shaft; threads on sheath that snap past prongs/flanges in instrument shaft shrouds; extrusion on instrument shaft shrouds that tube slides over; undercut on handle shrouds that tube slides into; grooves on outer tube that proximal hub on sheath snaps into; or combinations thereof.

In various embodiments, a trocar sheath may be configured to be used with an existing trocar (e.g., in a retrofit manner) or a trocar designed to be used with the trocar sheath.

In use, a surgeon or other user may insert the trocar 12 and obturator 14 into the tissue of a patient. After the blade 36 of the obturator 14 breaks through the tissue, the obturator 14 can be removed from the trocar 12. If a relatively small instrument is being used, the adapter 38 can be inserted. Otherwise, the instrument to be used can be inserted into the trocar sheath 52. The distal end of the instrument is inserted into the opening 24 of the trocar housing 18. When the distal end of the instrument extends through the second seal 32, a leak path is created through the second seal 32 and the unsealed distal portion of the instrument (e.g., the end effector of the instrument). Without the trocar sheath 52, the leak path would exist as long as the unsealed portion of the instrument extends through both the first seal 30 and the second seal 32 (i.e., until the sealed portion of the instrument reaches the first seal 30). With the trocar sheath, the leak path only exists from when the distal portion of the instrument passes through the second seal 32 and when the sheath cannula 54 reaches the first seal 30. Thus, the trocar sheath 52 reduces the amount of time that insufflation could be lost while the instrument is being inserted in the trocar 12. This reduction in time would be greater for instruments with longer unsealed portions (e.g., longer staplers). For some instruments, the trocar sheath 52 seals the trocar 12 before the end effector has exited the distal end 20 of the trocar cannula 16. This reduces or eliminates the likelihood of a loss of visualization due to insufflation loss while the end effector extends out of the trocar 12. To remove the instrument from the trocar 12, the trocar sheath 52 is removed with the instrument. If the instrument is removed first and the seal between the housing assembly 56 of the trocar sheath 52 is lost, insufflation loss would likely occur as long as the sheath cannula 54 extends through the second seal 32.

As previously stated, laparoscopic surgical devices having long end effectors can create leak paths in existing trocars, thereby resulting in the loss of adequate insufflation. A leak path is created when the two seals in existing trocars (i.e., the lip seal and the cross-slit valve) are both penetrated by the end portion of the laparoscopic surgical device. This leak path exists until the shaft of the surgical device reaches the lip seal. This problem has been recognized with existing 45 mm and 60 mm stapling devices having jaws that are long enough to penetrate both seals prior to reaching the shaft of the stapler.

The jaws of some stapling devices, such as the TITAN SGS from Standard Bariatrics, Inc., are approximately 250 mm long, thereby presenting two additional problems relating to insufflation leakage. First, the time required to insert the 250 mm long jaw of the TITAN SGS stapler is 4 to 5.5 times longer than what is required for existing 45 mm and 60 mm devices, which allows more air to leak from the insufflated volume prior to reaching the shaft portion of the inserted stapling instrument. If a significant volume of air is lost in the process of inserting the stapling instrument, visualization can be lost, leading to potential patient injury from inadvertent contact with patient anatomy during the period when visualization is not possible. Second, the length of the 250 mm jaw of the TITAN SGS device is great enough to exit the trocar in the intra-abdominal cavity prior to reaching the stapling instrument shaft and stopping insufflation air leakage. This is significant because if the surgeon were to insert the stapling instrument more quickly to minimize the volume of air leakage, the stapling instrument may exit the trocar in the intra-abdominal space in an uncontrolled manner, thereby leading to potential patient injury from inadvertent contact with patient anatomy.

Figure 12:
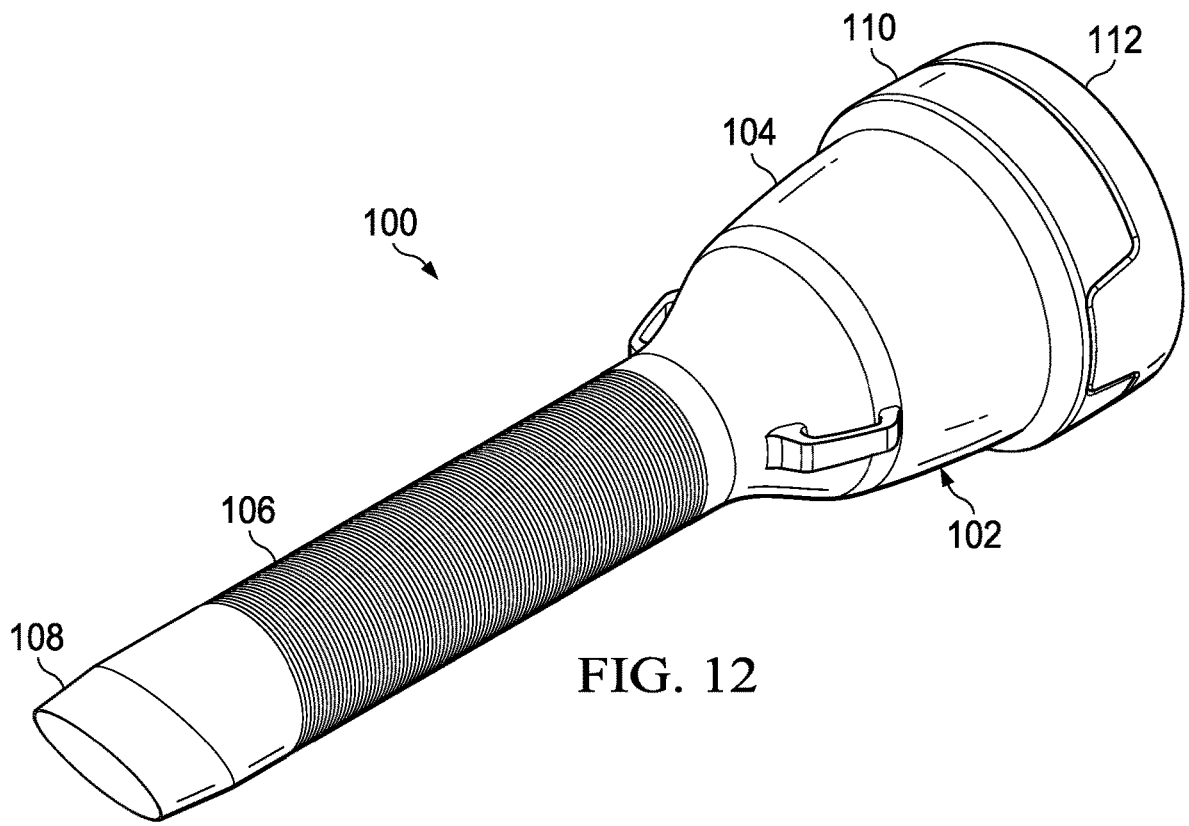
FIG. 12 is a perspective view of an example trocar showing the external components thereof.
Figure 13:
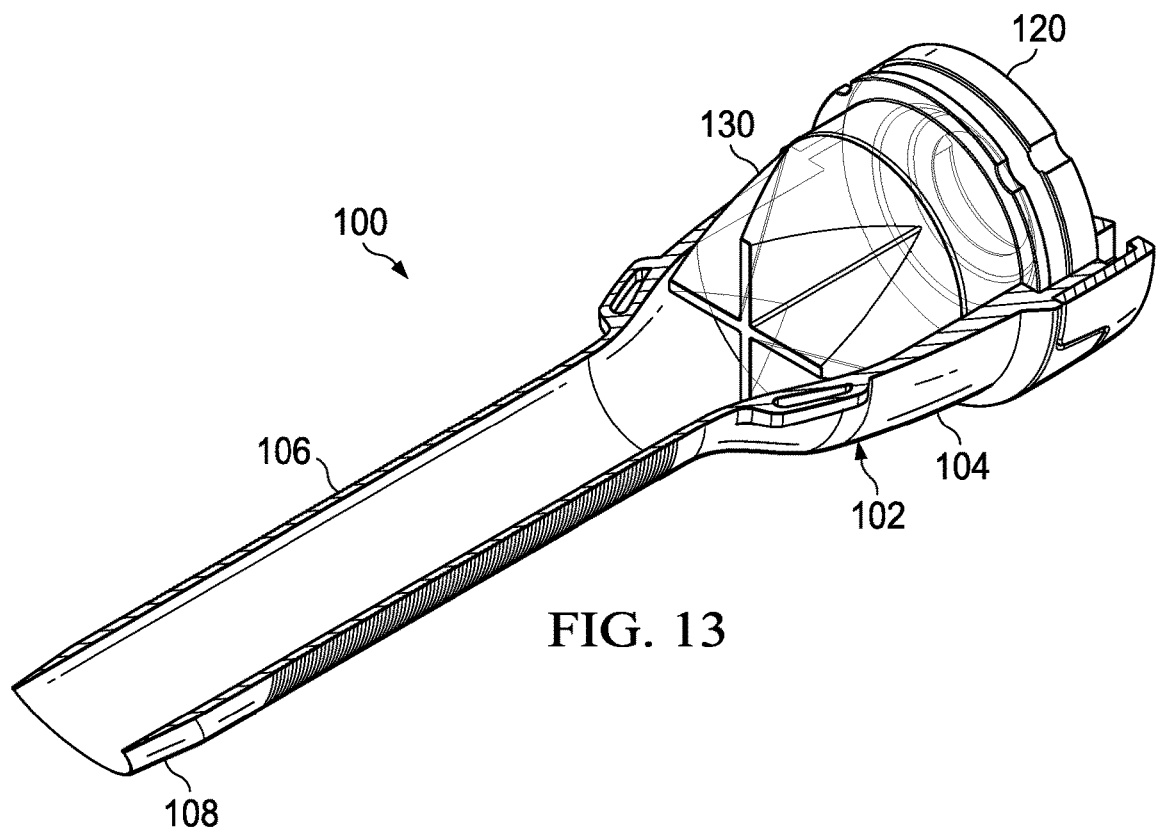
FIG. 13 is a cross-sectional view of the trocar of FIG. 12.

FIG. 12 provides a perspective view of example trocar 100, which includes cannula 102, lip 110 and cannula cap 112. Cannula 102 includes a tapered upper portion 104 and a tubular lower portion 106, wherein the internal diameter of upper portion 104 is greater than the internal diameter of lower portion 106, which terminates at angled tip 108. As previously described, a trocar such as that shown in FIG. 12 typically includes a seal and a valve that cooperate to maintain insufflation pressure during laparoscopic surgical procedures. The seal is typically a lip seal and the valve is a cross-slit valve. The lip seal maintains insufflation pressures after the shaft of a medical instrument has advanced past the seal and during instrument use in the surgical space. The cross-slit valve maintains insufflation when no instrument is present in the trocar. FIG. 13 provides a cross-sectional view of trocar 100, wherein lip seal 120 is visible underneath cannula cap 112 and cross-slit valve 130 is disposed within tapered upper portion 104 of cannula 102. The various implementations described below prevent air leakage during instrument insertion past lip seal 120 and cross-slit valve 130. Although cross-slit valve 130 is shown in the Figures, this valve may be unnecessary in implementations in which another valve disposed within the distal portion of the cannula prevents air leakage when the medical instrument is present in the cannula.

Figure 14:
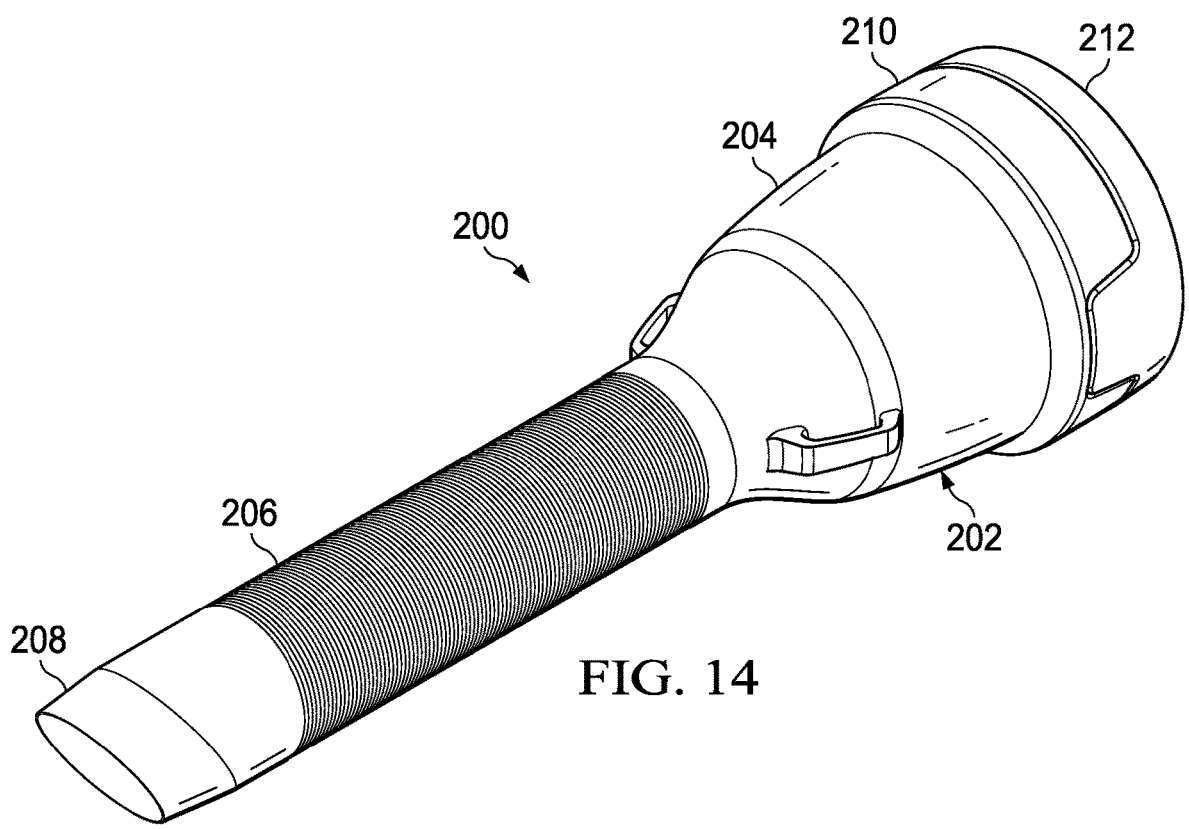
FIG. 14 is a perspective view of a trocar in accordance with a first implementation of the disclosed medical devices showing the external components thereof.
Figure 15:
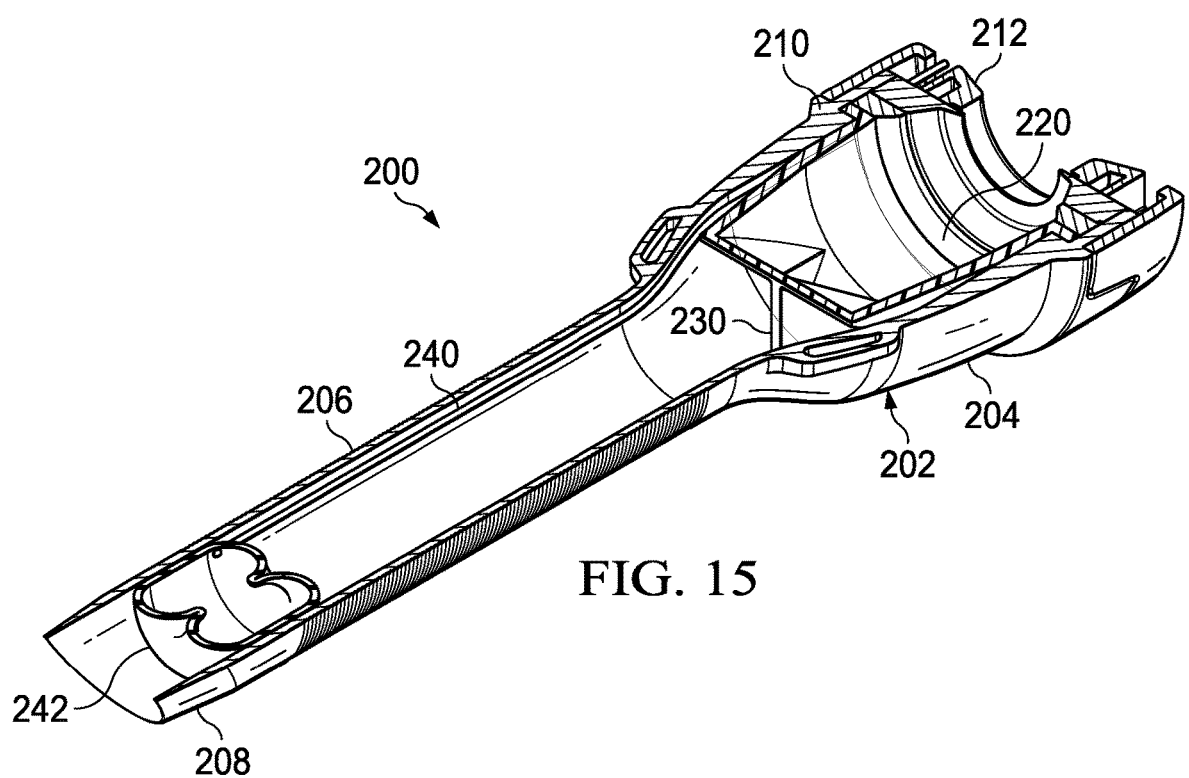
FIG. 15 is a cross-sectional view of the trocar of FIG. 14.

FIGS. 14 and 15 depict a distal balloon implementation, which minimizes air leakage during insertion of an instrument into a trocar when the cross-slit valve is opened and the shaft of the instrument has not reached the lip seal. FIG. 14 provides a perspective view of example trocar 200, which includes cannula 202, lip 210 and cannula cap 212. Cannula 202 includes a tapered upper portion 204 and a tubular lower portion 206, wherein the internal diameter of upper portion 204 is greater than the internal diameter of lower portion 206, which terminates at angled tip 208. FIG. 15 provides a cross-sectional view of trocar 200, wherein lip seal 220 is visible underneath cannula cap 212 and proximal cross-slit valve 230 is disposed within tapered upper portion 204 of cannula 202. Balloon pump tube 240, which inflates and deflates distal balloon 242, enters trocar 200 through cannula cap 212 and extends downward into tubular lower portion 206 of cannula 202 running parallel to the central axis of cannula 202. In this implementation, lip seal 220 is identical to that found in existing trocars and is designed to form a seal on the shaft of an instrument being inserted into the trocar 200. Proximal cross-slit valve 230 is also identical to that found in existing trocars and is designed to prevent air leaks when closed. Cannula 202 is also identical to that found in existing trocars and is designed to be a rigid tube which allows an instrument to be inserted through the tube for accessing the abdominal cavity. Cannula cap 212 is also identical to that found in existing trocars and is designed to retain lip seal 200 and proximal cross-slit valve 230 within cannula 202. Cannula cap 212 may also mate with other tools such as, for example, an obturator and a 5 mm adapter. Balloon pump tube 240 allows air to be pumped into and out of distal balloon 242, which is donut shaped and is located inside trocar 200 toward the distal end of the trocar. An instrument is pushed through the center of balloon 242, which deflates when the instrument is fully inserted. Alternative implementations include replacing the balloon with a self-inflating memory foam equivalent which would not require a balloon pump in order to inflate.

Figure 16:
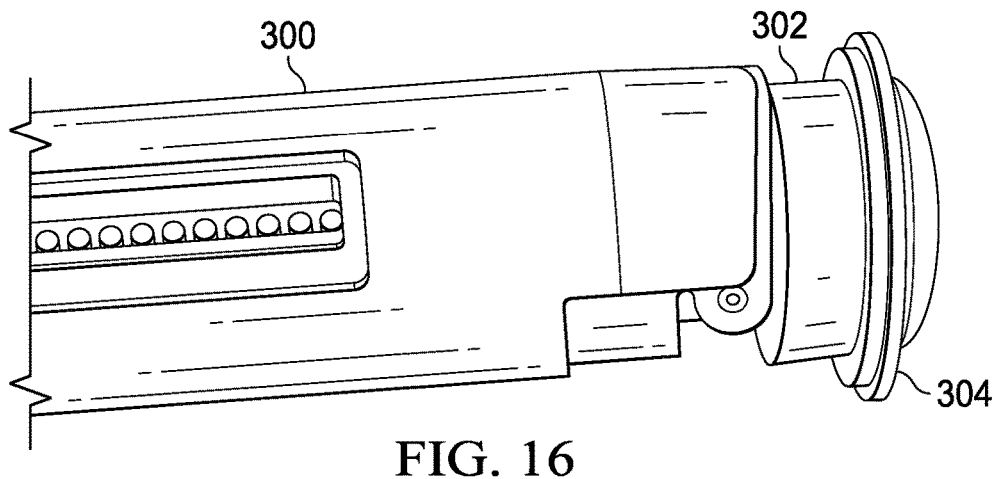
FIG. 16 is a perspective view of the distal end of a surgical stapling instrument to which a blunt end and seal have been attached.

FIG. 16 depicts a stapler distal seal implementation, which is a TITAN SGS surgical stapler accessory designed to minimize air leakage during insertion of the stapling instrument when the cross-slit valve is opened and the shaft of the instrument has not reached the trocar lip seal. As shown in FIG. 16, end effector 300 includes a pin at the distal end thereof which is used to pin blunt tip 302 to the end of the end effector. End effector lip seal 304 mates to the outer diameter of blunt tip 302 and fills the air gap between the outer diameter of blunt tip 302 and the inner diameter of the trocar cannula. Blunt tip 302 combined with end effector lip seal 304 permits the distal end of end effector 300 to be inserted all the way to the distal end of the trocar before air leakage occurs, thereby minimizing the time between when air leakage begins and the shaft of the stapling instrument reaches the trocar lip seal. In some implementations, this accessory is removable from end effector 300.

Figure 17:
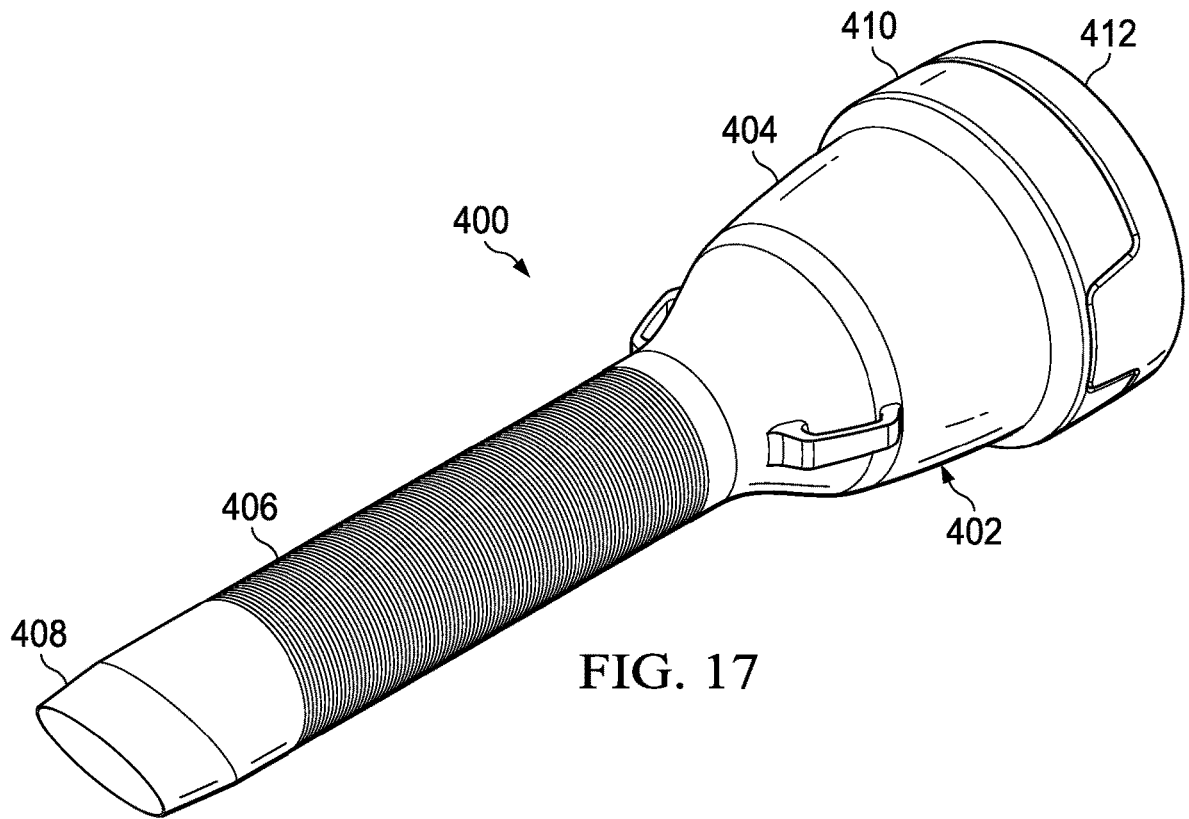
FIG. 17 is a perspective view of a trocar in accordance with a second implementation of the disclosed medical devices showing the external components thereof.
Figure 18:
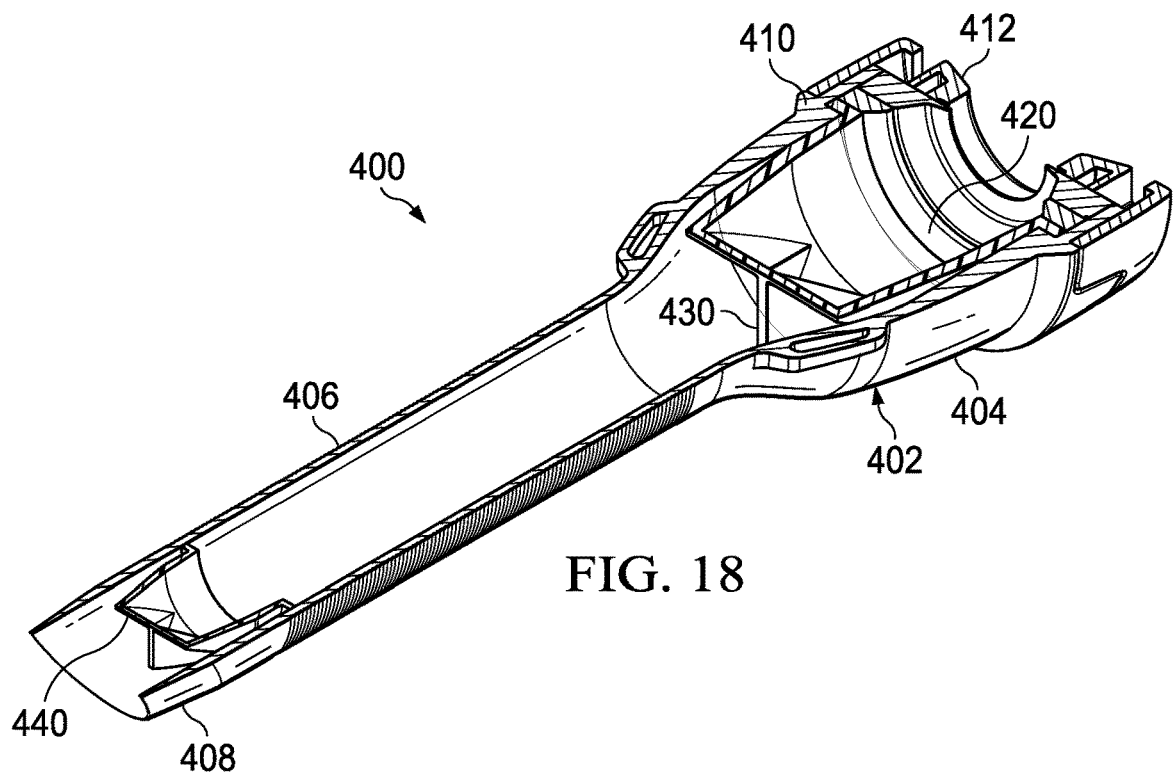
FIG. 18 is a cross-sectional view of the trocar of FIG. 17.

FIGS. 17 and 18 depict a distal seal implementation, which minimizes air leakage during insertion of an instrument into a trocar when the cross-slit valve is opened and the shaft of the instrument has not reached the lip seal. FIG. 17 provides a perspective view of example trocar 400, which includes cannula 402, lip 410 and cannula cap 412. Cannula 402 includes a tapered upper portion 404 and a tubular lower portion 406, wherein the internal diameter of upper portion 404 is greater than the internal diameter of lower portion 406, which terminates at tip 408. FIG. 15 provides a cross-sectional view of trocar 400, wherein lip seal 420 is visible underneath cannula cap 412 and proximal cross-slit valve 430 is disposed within tapered upper portion 404 of cannula 402. In various implementations, valve 430 is absent from cannula 402 as it is not necessary. Distal valve 440 is disposed within the distal portion of tubular lower portion 406. In this implementation, lip seal 420 is identical to that found in existing trocars and is designed to form a seal on the shaft of an instrument being inserted into the trocar 400. Proximal cross-slit valve 430 is also identical to that found in existing trocars and is designed to prevent air leaks when closed. Cannula 402 is also identical to that found in existing trocars and is designed to be a rigid tube which allows an instrument to be inserted through the tube for accessing the abdominal cavity. Cannula cap 412 is also identical to that found in existing trocars and is designed to retain lip seal 420 and proximal cross-slit valve 430 within cannula 402. Cannula cap 412 may also mate with other tools such as, for example, an obturator and a 5 mm adapter. Distal valve 440 prevents air leakage when closed. By placing valve 440 toward the distal end of trocar 400, an instrument can be inserted further into trocar cannula 402 before opening the valve and permitting air leakage, thereby minimizing the time between when the air leakage begins, and the shaft of the instrument reaches the lip seal. Distal valve 440 may be a cross-slit valve, trap door valve, dilating valve, or the like. One alternate implementation does not include proximal cross-slit valve 430 and another alternate implementation locates distal valve 440 entirely at the distal opening of trocar 400.

Figure 19A:
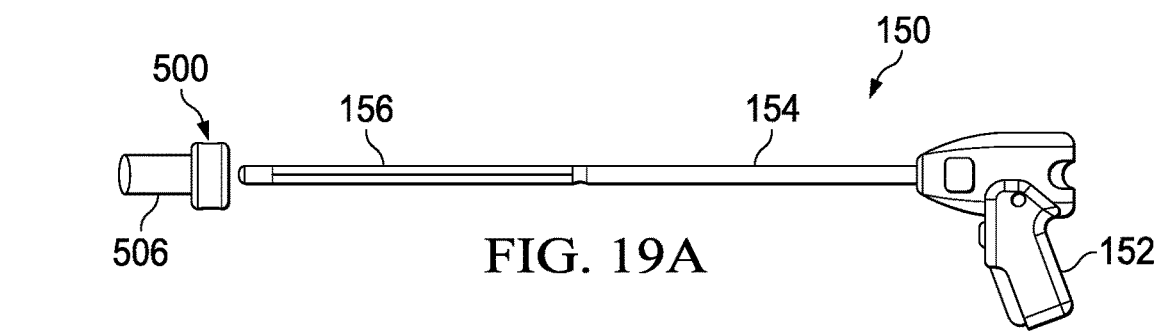
FIG. 19A depicts a hub according to an embodiment prior to the hub being placed on a stapling instrument.
Figure 19B:
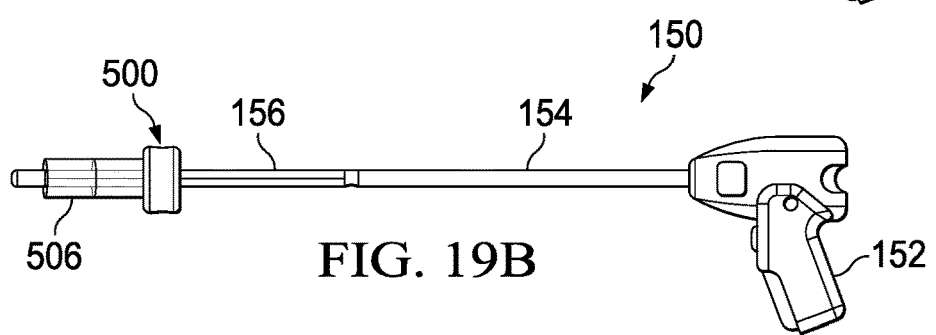
FIG. 19B depicts the hub placed on the stapling instrument of FIG. 19A showing a sleeve being partially extended along the length of the end effector of the stapling instrument.
Figure 19C:
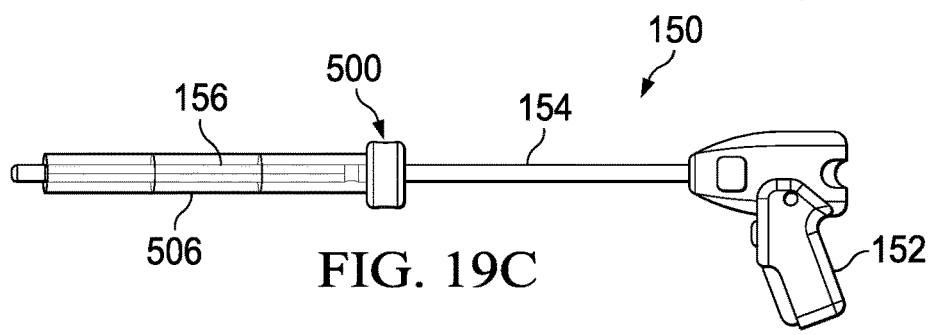
FIG. 19C depicts the sleeve of FIG. 19B fully extended along the length of the end effector such that it has reached the shaft of the stapling instrument.
Figure 20:
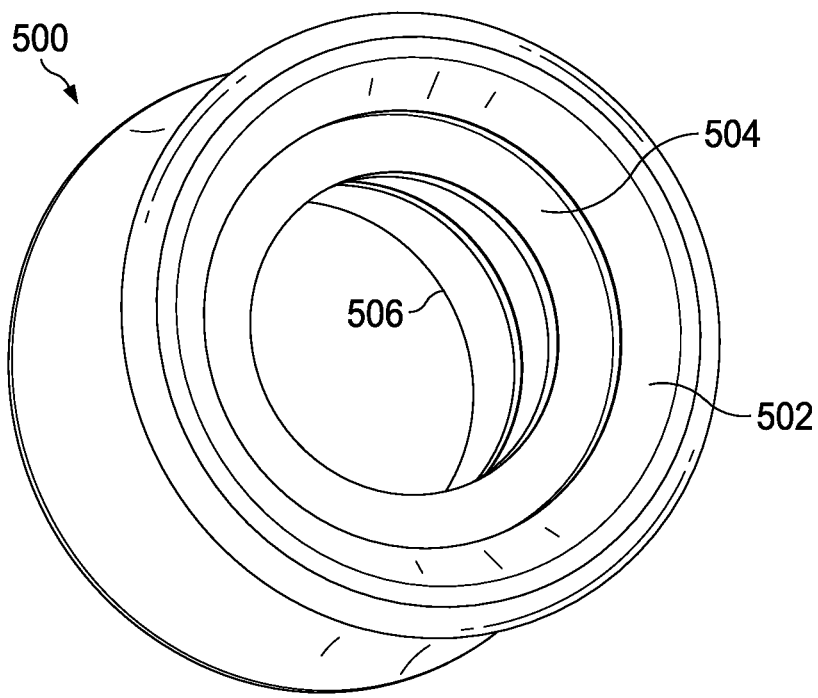
FIG. 20 is a perspective view of the hub of FIGS. 19A-19C, wherein the hub includes a retaining ring, a lip seal, and a telescopic sheath or sleeve.

FIGS. 19A-19C and 20 depict a telescoping sleeve implementation that includes an accessory that may be used in conjunction with existing trocar technology to eliminate air leakage during insertion of a stapling instrument into a trocar when the cross-slit valve is opened and shaft of the instrument has not reached the lip seal. As shown in FIGS. 19A-19C, stapling instrument 150 includes handle 152, shaft 154, and end effector 156. As shown in FIG. 20, hub 500 includes retaining ring 502, lip seal 504, and sheath or sleeve 506. In FIG. 19A, hub 500 has not yet been placed on end effector 156. In FIG. 19B, hub 500 has been placed on end effector 156 and sleeve 506 is shown partially extended along the length of end effector 156. In FIG. 19C, sleeve 506 has been fully extended along end effector 156 and has reached shaft 154 of stapling instrument 150. Hub 500 acts as a housing for internal components and also provides an exterior gripping surface for the user to slide sleeve 506 onto stapling instrument 150 and easily translate sleeve 506 along the axis of shaft 154. Lip seal 504 is similar to what is used in existing trocars and is designed to form a seal on the shaft of an instrument being inserted into the trocar. Another important aspect of this component is its drag force on the shaft of the stapling instrument. Lip seal 504 is designed to have less drag relative to the shaft of the instrument compared with the drag between the lip seal of the trocar and the sleeve. Retaining ring 502 houses and retains lip seal 504, an angled cap, and flared end of sleeve 506. Retaining ring 502 may be attached to hub 500 using ultrasonic welding, adhesives, a snap fit, or any other suitable attachment means. Retaining ring 502 provides enough axial preload on the components contained therein to create a hermetic seal that does not allow air leakage during use. Sleeve 506 is typically expandable thin wall rubber, low-density polyethylene (LDPE), or similar material which resides within hub 500 and includes two or more sections. Inserting a stapling instrument into the hub extends each section of sleeve 506 similar to a telescope so that the entire length of the stapling jaws is sealed.

Alternative implementations of the telescoping sleeve include a locking feature on hub 500 that locks the hub onto the proximal end of handle 152 when stapling instrument 150 is fully inserted into sleeve 506. This locking feature may include a quick-connect fitting, a radial compression spring that locks onto shaft 154, threads on hub or sleeve 506 that snap past prongs/flanges in the shrouds of handle 152, an extrusion on the handle shrouds over which a tube slides, an undercut on the handle shrouds that a tube slides into, and/or grooves on an outer tube that hub 500 on sleeve 506 snaps into. Additional variations include a locking feature on hub 500 that locks onto the proximal end of a trocar.

Figure 21:
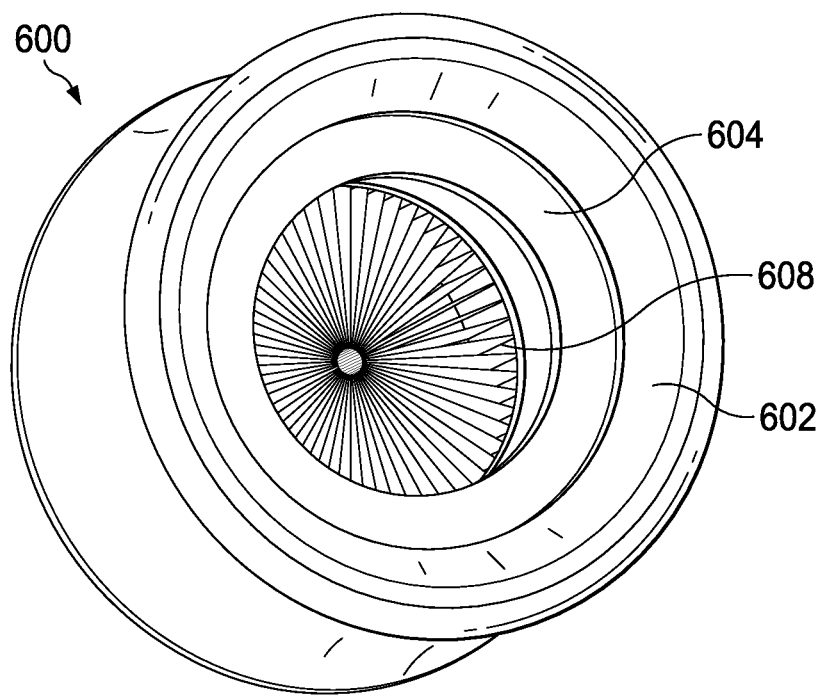
FIG. 21 is a perspective view of a hub according to an embodiment including a retaining ring, a lip seal, a telescopic sheath or sleeve, and a plurality of bristles mounted in a circular pattern within the hub.

FIG. 21 depicts a bristle valve implementation that includes an accessory that may be used in conjunction with existing trocar technology to eliminate air leakage during insertion of a stapling instrument into a trocar when the cross-slit valve is opened and shaft of the instrument has not reached the lip seal. Hub 600 acts as a housing for internal components and also provides an exterior gripping surface for the user to slide a sleeve onto a stapling instrument and easily translate the sleeve (e.g., sleeve 506) along the axis of the shaft of a stapling instrument. Lip seal 604 is similar to what is used in existing trocars and is designed to form a seal on the shaft of an instrument being inserted into the trocar. Another important aspect of this component is its drag force on the shaft of the stapling instrument. Lip seal 604 is designed to have less drag relative to the shaft of the instrument compared with the drag between the lip seal of the trocar and the sleeve. Retaining ring 602 houses and retains lip seal 604, an angled cap, and flared end of the sleeve. Retaining ring 602 may be attached to hub 600 using ultrasonic welding, adhesives, a snap fit, or any other suitable attachment means. Retaining ring 602 provides enough axial preload on the components contained therein to create a hermetic seal that does not allow air leakage during use. Bristles 608 line the inside of hub 600 in a circular pattern. When a stapling instrument is inserted into hub 600, bristles 608 fill any gap between the upper and lower jaws of the end effector component of the stapling instrument, which reduces the rate of any insufflation leaks as the stapling instrument is inserted through a trocar.

Alternative implementations of the bristle valve include a locking feature on hub 600 that locks the hub onto the proximal end of the handle of a stapling instrument when the instrument is fully inserted into the sleeve. This locking feature may include a quick-connect fitting, a radial compression spring that locks onto the shaft of the instrument, threads on the sleeve that snap past prongs/flanges in the shrouds of the handle, an extrusion on the handle shrouds over which a tube slides, an undercut on the handle shrouds that a tube slides into, and/or grooves on an outer tube that hub 600 on the sleeve snaps into. Additional variations include a locking feature on hub 560 that locks onto the proximal end of a trocar.

Figure 22A:
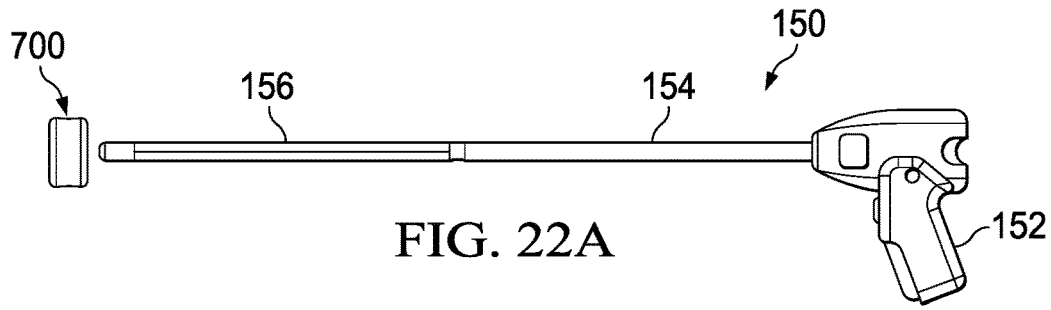
FIG. 22A depicts a hub according to an embodiment prior to the hub being placed on a stapling instrument.
Figure 22B:
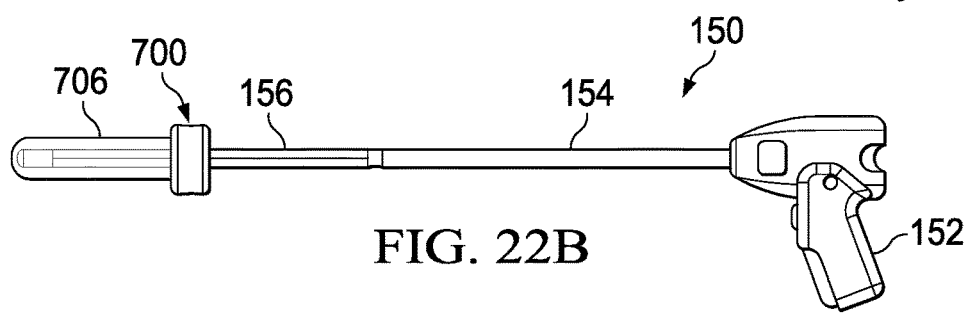
FIG. 22B depicts the hub placed on the stapling instrument of FIG. 19A showing a sheath being partially unrolled along the length of the end effector of the stapling instrument.
Figure 22C:
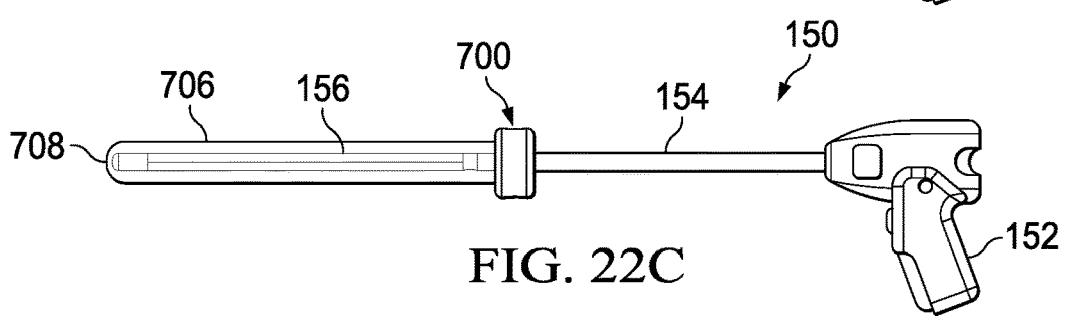
FIG. 22C depicts the sheath of FIG. 22B fully unrolled along the length of end effector such that it has reached the shaft of the stapling instrument.
Figure 23:
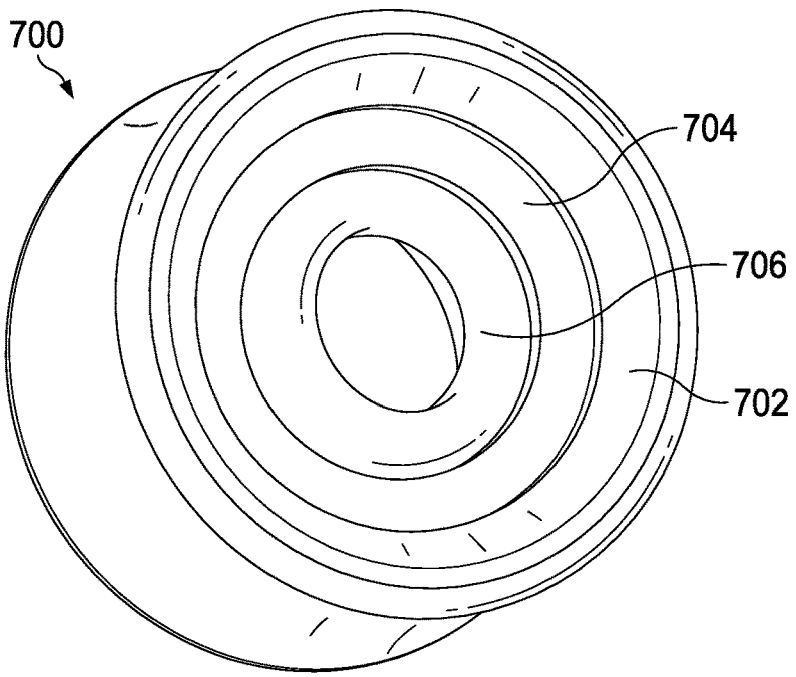
FIG. 23 depicts the hub of FIGS. 22A-22C, wherein the hub includes a retaining ring, a lip seal, and a sheath having an aperture formed therein.

FIGS. 22A-22C and 23 depict a rolled sheath implementation that includes an accessory that may be used in conjunction with existing trocar technology to eliminate air leakage during insertion of a stapling instrument into a trocar when the cross-slit valve is opened and shaft of the instrument has not reached the lip seal. As shown in FIGS. 22A-22C, stapling instrument 150 includes handle 152, shaft 154, and end effector 156. As shown in FIG. 23, hub 700 includes retaining ring 702, lip seal 704, and fully rolled sheath 706. In FIG. 22A, hub 700 has not yet been placed on end effector 156. In FIG. 19B, hub 700 has been placed on end effector 156 and sheath 706 is shown partially unrolled along the length of end effector 156. In FIG. 19C, sheath 706 has been fully unrolled along end effector 156 and has reached shaft 154 of stapling instrument 150. Hub 700 acts as a housing for internal components and also provides an exterior gripping surface for the user to slide sheath 706 onto stapling instrument 150 and easily translate sheath 706 along the axis of shaft 154. Lip seal 704 is similar to what is used in existing trocars and is designed to form a seal on the shaft of an instrument being inserted into the trocar. Another important aspect of this component is its drag force on the shaft of the stapling instrument. Lip seal 704 is designed to have less drag relative to the shaft of the instrument compared with the drag between the lip seal of the trocar and the sheath. Retaining ring 702 houses and retains lip seal 704, an angled cap, and flared end of sheath 706. Retaining ring 702 may be attached to hub 700 using ultrasonic welding, adhesives, a snap fit, or any other suitable attachment means. Retaining ring 702 provides enough axial preload on the components contained therein to create a hermetic seal that does not allow air leakage during use. Sheath 706 is typically expandable thin wall rubber, low-density polyethylene (LDPE), or similar material which resides within hub 700. Inserting stapling instrument 150 into hub 700 unrolls sheath 706 as the instrument is inserted such that the entire length of the jaws of end effector 156 is sealed when the instrument is fully inserted. An aperture 708 formed in the distal end of sheath 706 allows an instrument to be pushed therethrough by expanding around the end-effector.

Alternative implementations of the rolled sheath include a locking feature on hub 700 that locks the hub onto the proximal end of handle 152 when stapling instrument 150 is fully inserted into sheath 706. This locking feature may include a quick-connect fitting, a radial compression spring that locks onto shaft 154, threads on sheath 706 that snap past prongs/flanges in the shrouds of handle 152, an extrusion on the handle shrouds over which a tube slides, an undercut on the handle shrouds that a tube slides into, and/or grooves on an outer tube that hub 700 on sheath 706 snaps into. Additional variations include a locking feature on hub 700 that locks onto the proximal end of a trocar.

Figure 24:
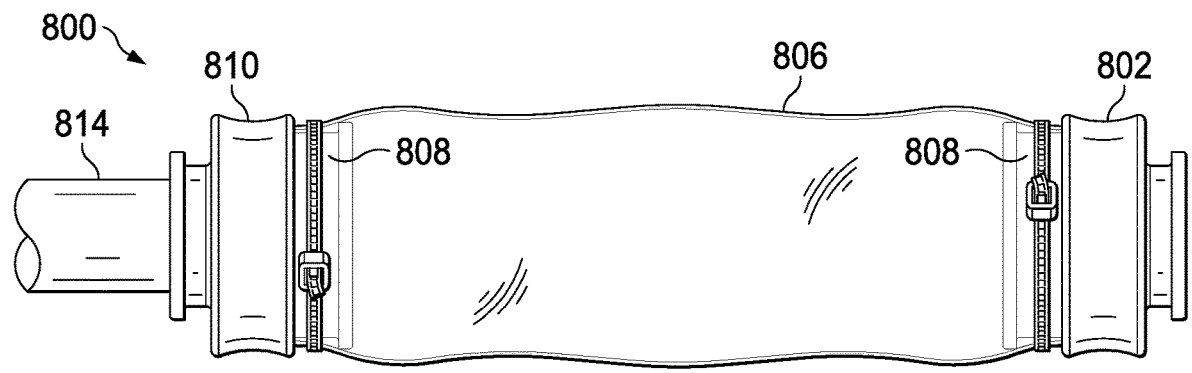
FIG. 24 is a side view of a collapsible sleeve assembly according to an embodiment.
Figure 25:
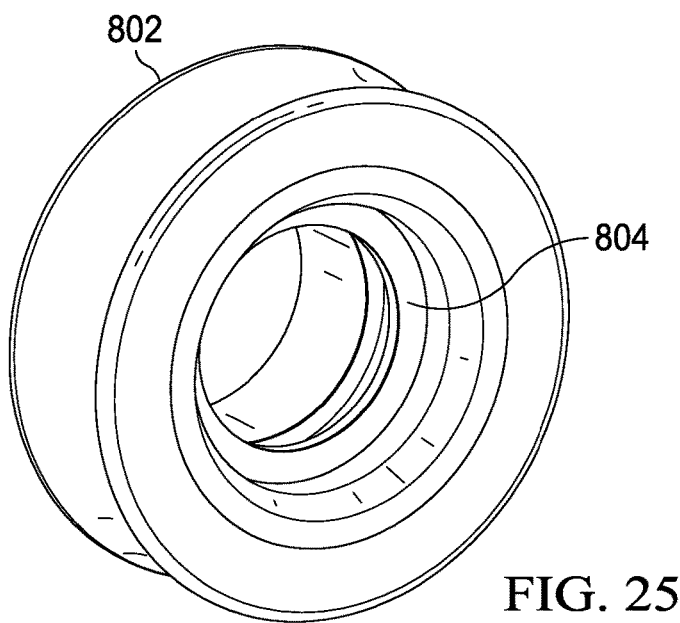
FIG. 25 is a perspective view of the internal components of the proximal hub of the collapsible sleeve assembly of FIG. 24.
Figure 26:
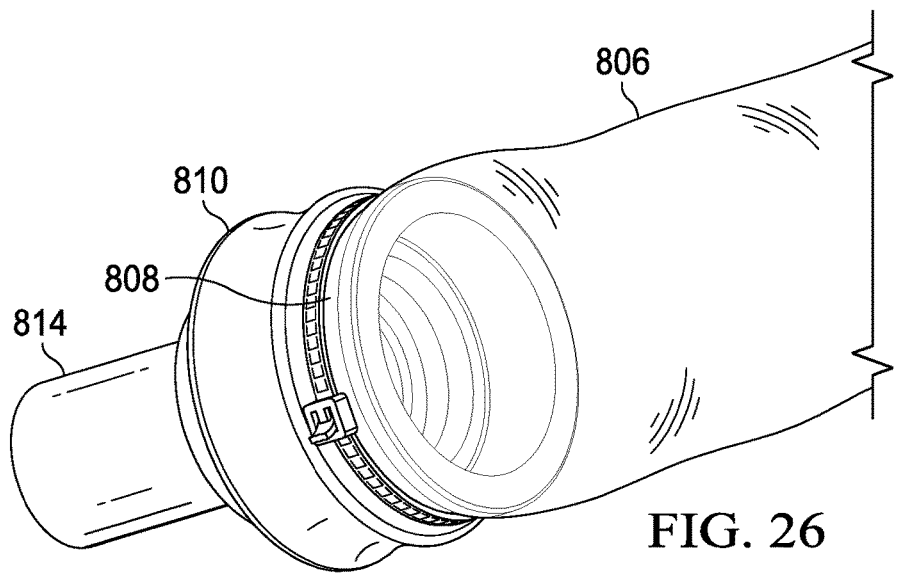
FIG. 26 is a perspective view of the internal components of the trocar mating hub component of the collapsible sleeve assembly of FIG. 24.

FIGS. 24-26 depict a collapsible sleeve assembly implementation that includes an accessory that may be used in conjunction with existing trocar technology to eliminate air leakage during insertion of a stapling instrument into a trocar when the cross-slit valve is opened and shaft of the instrument has not reached the lip seal. As best shown in FIG. 24, collapsible sleeve assembly 800 includes proximal hub 802 which houses lip seal 804, sleeve 806, sleeve mating structures 808, trocar mating hub 810 which houses a lip seal, and sheath 814 attached thereto. Proximal hub 802 acts as a housing for internal components and also provides an exterior gripping surface for the user to slide sleeve 806 onto a stapling instrument and easily translate sleeve 806 along the axis of the shaft of a stapling instrument. Lip seal 804 is similar to what is used in existing trocars and is designed to form a seal on the shaft of an instrument being inserted into the trocar. Another important aspect of this component is its drag force on the shaft of the stapling instrument. Sleeve 806 is a thin walled bag made from low-density polyethylene (LDPE) or similar material that is thin enough to collapse when compressed and to expand without ripping when pulled under tension. Trocar mating hub 810 acts as a housing in which to mount internal components and also provides an exterior gripping surface for the user when sliding collapsible sleeve 800 into a trocar. Trocar mating hub 810 remains flush with the trocar when inserted into the trocar. Sleeve mating structures 808 cooperate with sleeve 806 to create an airtight seal around trocar mating hub 810 and proximal hub 802. Sheath 814 is a thin walled tube made from high-density polyethylene (HDPE) or similar material that is rigid enough to not collapse during use while thin enough to not significantly increase the internal diameter of the trocar. In an example implementation, the wall thickness of the sheath is about 0.008" thick. Sheath 814 is designed to have more drag relative to the trocar lip seal than the drag between lip seal 804 in trocar mating hub 810 and the stapling instrument.

Alternative implementations of the collapsible sleeve assembly include a locking feature on proximal hub 802 that locks the hub onto the proximal end of the handle of a stapling instrument when the instrument is fully inserted into sleeve 806. This locking feature may include a quick-connect fitting, a radial compression spring that locks onto the shaft of the instrument, threads on sleeve 806 that snap past prongs/flanges in the shrouds of the handle, an extrusion on the handle shrouds over which a tube slides, an undercut on the handle shrouds that a tube slides into, and/or grooves on an outer tube that proximal hub 802 on sleeve 806 snaps into.

As previously stated and as used herein, the singular forms "a," "an," and "the," refer to both the singular as well as plural, unless the context clearly indicates otherwise. The term "comprising" as used herein is synonymous with "including," "containing," or "characterized by," and is inclusive or open-ended and does not exclude additional, unrecited elements or method steps. Although many methods and materials similar or equivalent to those described herein can be used, particular suitable methods and materials are described herein. Unless context indicates otherwise, the recitations of numerical ranges by endpoints include all numbers subsumed within that range. Furthermore, references to "one implementation" are not intended to be interpreted as excluding the existence of additional implementations that also incorporate the recited features. Moreover, unless explicitly stated to the contrary, implementations "comprising" or "having" an element or a plurality of elements having a particular property may include additional elements whether or not they have that property.

The terms "substantially" and "about" used throughout this specification are used to describe and account for small fluctuations, such as due to variations in processing. For example, these terms can refer to less than or equal to ±5%, such as less than or equal to ±2%, such as less than or equal to ±1%, such as less than or equal to ±0.5%, such as less than or equal to ±0.2%, such as less than or equal to ±0.1%, such as less than or equal to ±0.05%, and/or 0%.

There may be many alternate ways to implement the disclosed inventive subject matter. Various functions and elements described herein may be partitioned differently from those shown without departing from the scope of the disclosed inventive subject matter. Generic principles defined herein may be applied to other implementations. Different numbers of a given module or unit may be employed, a different type or types of a given module or unit may be employed, a given module or unit may be added, or a given module or unit may be omitted.

While several devices and components thereof have been discussed in detail above, it should be understood that the components, features, configurations, and methods of using the devices discussed are not limited to the contexts provided above. In particular, components, features, configurations, and methods of use described in the context of one of the other devices may be incorporated into any of the other devices. Furthermore, not limited to the further description provided below, additional and alternative suitable components, features, configurations, and methods of using the devices, as well as various ways in which the teachings herein may be combined and interchanged, will be apparent to those of ordinary skill in the art in view of the teachings herein.

Versions of the devices described above may be actuated mechanically or electromechanically (e.g., using one or more electrical motors, solenoids, etc.). However, other actuation modes may be suitable as well including but not limited to pneumatic and/or hydraulic actuation, etc. Various suitable ways in which such alternative forms of actuation may be provided in a device as described above will be apparent to those of ordinary skill in the art in view of the teachings herein.

Versions of the devices described above may have various types of construction. By way of example only, any of the devices described herein, or components thereof, may be constructed from a variety of metal and/or plastic materials.

Having shown and described various versions in the present disclosure, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, versions, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

What is claimed is:

1. A trocar assembly, comprising:
    a trocar sheath slidably and removably extendable within a trocar having a trocar housing and a trocar cannula, wherein the trocar sheath comprises:
        a sheath cannula defining an interior lumen having an open distal end and an open proximal end; and
        a housing assembly comprising a sheath hub coupled to the open proximal end of the sheath cannula, and a sheath seal contained in the sheath hub,
    wherein when the sheath cannula is positioned in the trocar, the sheath cannula extends beyond a distal end of the trocar cannula; and
    an obturator separate from the trocar sheath, comprising a handle and a distal blade, wherein the obturator is slidably and removably extendable within the trocar, and when the obturator is inserted in the trocar, the handle abuts the trocar housing.

2. The trocar assembly of claim 1, wherein the trocar comprises a trocar seal assembly and, when the trocar sheath is positioned in the trocar, the trocar seal assembly cooperates with the trocar sheath to sealingly engage an outer surface of the trocar sheath.

3. The trocar assembly of claim 1, wherein a first drag on an instrument being inserted through the sheath seal is less than a second drag on the instrument being removed through the sheath seal.

4. The trocar assembly of claim 1, wherein, when an instrument is positioned in the trocar sheath, the housing assembly of the trocar sheath cooperates with the instrument to sealingly engage an outer surface of the instrument.

5. The trocar assembly of claim 1, wherein the housing assembly further comprises a seal plate positioned in the sheath hub and coupled to an interior of the open proximal end of the sheath cannula.

6. The trocar assembly of claim 5, wherein the open proximal end of the sheath cannula has an outwardly flared portion that corresponds to a flared portion of the seal plate.

7. The trocar assembly of claim 1, wherein the sheath hub is coupled to an exterior of the open proximal end of the sheath cannula.

8. The trocar assembly of claim 1, wherein the sheath seal is a lip seal.

9. The trocar assembly of claim 1, wherein the housing assembly further comprises a sheath cap contained in the sheath hub proximal of the sheath seal.

10. The trocar assembly of claim 9, wherein the sheath cap is configured to provide an axial preload on the open proximal end of the sheath cannula and the sheath seal to provide a hermetic seal.

11. The trocar assembly of claim 1, wherein a thickness of the sheath cannula is in a range of 0.005 inches to 0.01 inches.

12. The trocar assembly of claim 1, wherein the trocar sheath is positioned in the trocar.

13. The trocar assembly of claim 1, wherein the trocar assembly is a retrofit trocar assembly.

14. A kit comprising the trocar assembly of claim 1, wherein the trocar further comprises a trocar seal assembly.

15. The kit of claim 14, further comprising an adapter configured to be inserted into an opening of the trocar housing, the adaptor having an opening smaller than the opening of the trocar housing.

16. The kit of claim 15, wherein the adapter includes an adapter housing and an adapter cannula and, when the adapter is inserted in the trocar, the adapter housing abuts the trocar housing, and a distal end of the adapter cannula extends into and is fluidically coupled with the trocar cannula.

* * * * *